(12) United States Patent  
Modesitt

(10) Patent No.: US 7,678,133 B2
(45) Date of Patent: Mar. 16, 2010

(54) BIOLOGICAL TISSUE CLOSURE DEVICE AND METHOD

(75) Inventor: D. Bruce Modesitt, San Carlos, CA (US)

(73) Assignee: Arstasis, Inc., San Carlos, CA (US)

( * ) Notice: Subject to any disclaimer, the term of this patent is extended or adjusted under 35 U.S.C. 154(b) by 1201 days.

(21) Appl. No.: 10/888,682

(22) Filed: Jul. 10, 2004

(65) Prior Publication Data

US 2006/0009802 A1 Jan. 12, 2006

(51) Int. Cl.
*A61B 17/08* (2006.01)
*A61B 18/18* (2006.01)
*A61B 18/04* (2006.01)

(52) U.S. Cl. .................. 606/216; 606/214; 606/27; 606/41

(58) Field of Classification Search ............. 606/27–32, 606/41, 48–50, 213–316; 128/898
See application file for complete search history.

(56) References Cited

U.S. PATENT DOCUMENTS

| | | | |
|---|---|---|---|
| 3,730,185 A | 5/1973 | Cook et al. | |
| 4,006,747 A | 2/1977 | Kronenthal et al. | |
| 4,744,364 A | 5/1988 | Kensey | |
| 4,774,949 A | 10/1988 | Fogarty | |
| 4,890,611 A | 1/1990 | Monfort et al. | |
| 4,921,484 A | 5/1990 | Hillstead | |
| 4,962,755 A | 10/1990 | King et al. | |
| 5,183,464 A | 2/1993 | Dubrul et al. | |
| 5,304,184 A | 4/1994 | Hathaway et al. | |
| 5,336,221 A * | 8/1994 | Anderson | 606/27 |
| 5,358,507 A | 10/1994 | Daily | |
| 5,364,389 A * | 11/1994 | Anderson | 606/8 |
| 5,368,601 A | 11/1994 | Sauer et al. | |
| 5,391,182 A | 2/1995 | Chin | |
| 5,391,183 A | 2/1995 | Janzen et al. | |
| 5,403,329 A | 4/1995 | Hinchcliffe | |
| 5,415,657 A | 5/1995 | Taymor-Luria | |
| 5,417,699 A | 5/1995 | Klein et al. | |
| 5,437,665 A | 8/1995 | Munro | |
| 5,439,469 A | 8/1995 | Heaven et al. | |
| 5,451,230 A | 9/1995 | Steinert | |
| 5,462,561 A | 10/1995 | Voda | |
| 5,467,786 A | 11/1995 | Allen et al. | |
| 5,470,338 A | 11/1995 | Whitfield et al. | |
| 5,474,568 A | 12/1995 | Scott | |
| 5,476,470 A | 12/1995 | Fitzgibbons, Jr. | |
| 5,489,288 A | 2/1996 | Buelna | |
| 5,496,332 A | 3/1996 | Sierra et al. | |
| 5,496,334 A | 3/1996 | Klundt et al. | |
| 5,503,634 A | 4/1996 | Christy | |
| 5,507,744 A * | 4/1996 | Tay et al. | 606/50 |

(Continued)

FOREIGN PATENT DOCUMENTS

WO WO 03/082363 A2 10/2003

(Continued)

OTHER PUBLICATIONS

International Search Report, mailed Aug. 20, 2007, for PCT Application No. PCT/US06/18915 filed on May 12, 2006, 2 pages.

(Continued)

*Primary Examiner*—Michael Peffley
(74) *Attorney, Agent, or Firm*—Morrison & Foerster LLP

(57) ABSTRACT

Devices and methods for biological tissue closure are disclosed. Arteriotomy closure and hemostasis devices and methods are disclosed. A device that can provide a lateral tension across an opening in the tissue and apply energy to seal the tissue is disclosed. Methods for using the device are also disclosed.

28 Claims, 16 Drawing Sheets

U.S. PATENT DOCUMENTS

| | | | |
|---|---|---|---|
| 5,527,321 A | 6/1996 | Hinchliffe | |
| 5,527,322 A | 6/1996 | Klein et al. | |
| 5,571,169 A | 11/1996 | Plaia et al. | |
| 5,613,974 A | 3/1997 | Andreas et al. | |
| 5,620,461 A | 4/1997 | Muijs Van De Moer et al. | |
| 5,622,188 A | 4/1997 | Plaia et al. | |
| 5,645,566 A | 7/1997 | Brenneman et al. | |
| 5,653,717 A | 8/1997 | Ko et al. | |
| 5,695,504 A | 12/1997 | Gifford, III et al. | |
| 5,700,273 A | 12/1997 | Buelna et al. | |
| 5,709,224 A * | 1/1998 | Behl et al. | 128/898 |
| 5,746,755 A | 5/1998 | Wood et al. | |
| 5,762,066 A | 6/1998 | Law et al. | |
| 5,766,183 A | 6/1998 | Sauer | |
| 5,772,673 A | 6/1998 | Cuny et al. | |
| 5,779,719 A | 7/1998 | Klein et al. | |
| 5,792,152 A | 8/1998 | Klein et al. | |
| 5,797,929 A | 8/1998 | Andreas et al. | |
| 5,817,108 A | 10/1998 | Poncet | |
| 5,830,232 A | 11/1998 | Hasson | |
| 5,836,955 A | 11/1998 | Buelna et al. | |
| 5,846,253 A | 12/1998 | Buelna et al. | |
| 5,860,990 A | 1/1999 | Nobles et al. | |
| 5,860,991 A | 1/1999 | Klein et al. | |
| 5,868,762 A | 2/1999 | Cragg et al. | |
| 5,882,302 A | 3/1999 | Driscoll, Jr. et al. | |
| 5,902,311 A | 5/1999 | Andreas et al. | |
| 5,921,994 A | 7/1999 | Andreas et al. | |
| 5,941,897 A | 8/1999 | Myers | |
| 5,954,732 A | 9/1999 | Hart et al. | |
| 5,972,005 A | 10/1999 | Stalker et al. | |
| 5,980,539 A | 11/1999 | Kontos | |
| 5,984,917 A | 11/1999 | Fleischman et al. | |
| 5,984,948 A | 11/1999 | Hasson | |
| 5,984,950 A | 11/1999 | Cragg et al. | |
| 6,033,401 A | 3/2000 | Edwards et al. | |
| 6,036,699 A | 3/2000 | Andreas et al. | |
| 6,036,721 A | 3/2000 | Harren et al. | |
| 6,042,601 A | 3/2000 | Smith | |
| 6,063,085 A | 5/2000 | Tay et al. | |
| 6,071,292 A | 6/2000 | Makower et al. | |
| 6,071,300 A | 6/2000 | Brenneman et al. | |
| 6,093,173 A | 7/2000 | Balceta et al. | |
| 6,117,144 A | 9/2000 | Nobles et al. | |
| 6,117,145 A | 9/2000 | Wood et al. | |
| 6,136,010 A | 10/2000 | Modesitt et al. | |
| 6,143,004 A | 11/2000 | Davis et al. | |
| 6,146,397 A | 11/2000 | Harkrider, Jr. | |
| 6,152,918 A | 11/2000 | Padilla et al. | |
| 6,159,232 A | 12/2000 | Nowakowski | |
| 6,171,317 B1 | 1/2001 | Jackson et al. | |
| 6,179,832 B1 * | 1/2001 | Jones et al. | 606/32 |
| 6,190,396 B1 | 2/2001 | Whitin et al. | |
| 6,197,042 B1 | 3/2001 | Ginn et al. | |
| 6,203,554 B1 | 3/2001 | Roberts | |
| 6,206,893 B1 | 3/2001 | Klein et al. | |
| 6,206,895 B1 | 3/2001 | Levinson | |
| 6,245,079 B1 | 6/2001 | Nobles et al. | |
| 6,258,084 B1 * | 7/2001 | Goldman et al. | 606/32 |
| 6,302,898 B1 * | 10/2001 | Edwards et al. | 606/214 |
| 6,358,244 B1 | 3/2002 | Newman et al. | |
| 6,358,556 B1 | 3/2002 | Ding et al. | |
| 6,371,975 B2 | 4/2002 | Cruise et al. | |
| 6,383,208 B1 | 5/2002 | Sancoff et al. | |
| 6,395,015 B1 | 5/2002 | Borst et al. | |
| 6,398,782 B1 | 6/2002 | Pecor et al. | |
| 6,454,777 B1 | 9/2002 | Green | |
| 6,457,182 B1 | 10/2002 | Szczesuil et al. | |
| 6,458,147 B1 | 10/2002 | Cruise et al. | |
| 6,468,228 B1 | 10/2002 | Topel et al. | |
| 6,475,182 B1 | 11/2002 | Hnojewyj et al. | |
| 6,506,210 B1 | 1/2003 | Kanner | |
| 6,517,553 B2 | 2/2003 | Klein et al. | |
| 6,524,321 B2 | 2/2003 | Kanesaka | |
| 6,533,795 B1 | 3/2003 | Tran et al. | |
| 6,562,059 B2 | 5/2003 | Edwards et al. | |
| 6,565,583 B1 | 5/2003 | Deaton et al. | |
| 6,623,510 B2 | 9/2003 | Carley et al. | |
| 6,626,855 B1 | 9/2003 | Weng et al. | |
| 6,641,592 B1 | 11/2003 | Sauer et al. | |
| 6,656,136 B1 | 12/2003 | Weng et al. | |
| 6,663,655 B2 | 12/2003 | Ginn et al. | |
| 6,682,489 B2 | 1/2004 | Tenerz et al. | |
| 6,719,694 B2 | 4/2004 | Weng et al. | |
| 6,719,750 B2 | 4/2004 | Varner et al. | |
| 6,733,515 B1 | 5/2004 | Edwards et al. | |
| 6,743,195 B2 | 6/2004 | Zucker et al. | |
| 6,749,621 B2 | 6/2004 | Pantages et al. | |
| 6,749,622 B2 | 6/2004 | McGuckin, Jr. et al. | |
| 6,767,356 B2 | 7/2004 | Kanner et al. | |
| 6,773,699 B1 | 8/2004 | Soltz et al. | |
| 6,780,197 B2 | 8/2004 | Roe et al. | |
| 6,790,220 B2 | 9/2004 | Morris et al. | |
| 6,802,822 B1 | 10/2004 | Dodge | |
| 6,818,008 B1 | 11/2004 | Cates et al. | |
| 6,840,952 B2 | 1/2005 | Saker et al. | |
| 6,846,319 B2 | 1/2005 | Ginn et al. | |
| 6,846,320 B2 | 1/2005 | Ashby et al. | |
| 6,846,321 B2 | 1/2005 | Zucker et al. | |
| 6,860,895 B1 | 3/2005 | Akerfeldt et al. | |
| 6,863,680 B2 | 3/2005 | Ashby | |
| 6,890,342 B2 | 5/2005 | Zhu et al. | |
| 6,890,343 B2 | 5/2005 | Ginn et al. | |
| 6,890,344 B2 | 5/2005 | Levinson | |
| 6,893,431 B2 | 5/2005 | Naimark et al. | |
| 6,896,692 B2 | 5/2005 | Ginn et al. | |
| 6,929,655 B2 | 8/2005 | Egnelov et al. | |
| 6,936,053 B1 | 8/2005 | Weiss | |
| 6,939,348 B2 | 9/2005 | Malecki et al. | |
| 6,939,357 B2 | 9/2005 | Navarro et al. | |
| 6,939,363 B2 | 9/2005 | Akerfeldt et al. | |
| 6,939,364 B1 | 9/2005 | Soltz et al. | |
| 6,942,674 B2 | 9/2005 | Belef et al. | |
| 6,949,080 B2 | 9/2005 | Wolf et al. | |
| 6,949,107 B2 | 9/2005 | McGuckin, Jr. et al. | |
| 6,949,114 B2 | 9/2005 | Milo et al. | |
| 6,964,668 B2 | 11/2005 | Modesitt et al. | |
| 6,969,397 B2 | 11/2005 | Ginn | |
| 6,981,983 B1 | 1/2006 | Rosenblatt et al. | |
| 6,994,686 B2 | 2/2006 | Cruise et al. | |
| 7,001,400 B1 | 2/2006 | Modesitt et al. | |
| 7,008,440 B2 | 3/2006 | Sing et al. | |
| 7,008,442 B2 | 3/2006 | Brightbill | |
| 7,025,746 B2 | 4/2006 | Tal | |
| 7,025,776 B1 | 4/2006 | Houser et al. | |
| 7,029,489 B1 | 4/2006 | Ashby et al. | |
| 7,037,322 B1 | 5/2006 | Sing et al. | |
| 7,037,323 B2 | 5/2006 | Sing et al. | |
| 7,041,119 B2 | 5/2006 | Green | |
| 7,074,232 B2 | 7/2006 | Kanner et al. | |
| 7,077,848 B1 | 7/2006 | de Juan, Jr. et al. | |
| 7,186,251 B2 * | 3/2007 | Malecki et al. | 606/41 |
| 7,235,087 B2 | 6/2007 | Modesitt et al. | |
| 7,247,162 B1 | 7/2007 | Thornton | |
| 7,335,220 B2 | 2/2008 | Khosravi et al. | |
| 2001/0031922 A1 | 10/2001 | Weng et al. | |
| 2001/0047165 A1 | 11/2001 | Makower et al. | |
| 2002/0016614 A1 | 2/2002 | Klein et al. | |
| 2002/0062146 A1 | 5/2002 | Makower et al. | |
| 2002/0156495 A1 | 10/2002 | Brenneman et al. | |
| 2003/0093093 A1 | 5/2003 | Modesitt et al. | |
| 2003/0100921 A1 | 5/2003 | Addis et al. | |
| 2003/0158578 A1 | 8/2003 | Pantages et al. | |
| 2003/0233120 A1 | 12/2003 | Akerfeldt | |

| | | |
|---|---|---|
| 2004/0044350 A1 | 3/2004 | Martin et al. |
| 2004/0092964 A1 | 5/2004 | Modesitt et al. |
| 2004/0097978 A1 | 5/2004 | Modesitt et al. |
| 2004/0122449 A1 | 6/2004 | Modesitt et al. |
| 2004/0138522 A1 | 7/2004 | Haarstad et al. |
| 2004/0143290 A1 | 7/2004 | Brightbill |
| 2004/0153123 A1 | 8/2004 | Palermo et al. |
| 2004/0158287 A1 | 8/2004 | Cragg et al. |
| 2004/0172058 A1 | 9/2004 | Edwards et al. |
| 2004/0176758 A1 | 9/2004 | Yassinzadeh |
| 2004/0215232 A1 | 10/2004 | Belhe et al. |
| 2004/0220604 A1 | 11/2004 | Fogarty et al. |
| 2004/0267307 A1 | 12/2004 | Bagaoisan et al. |
| 2004/0267308 A1 | 12/2004 | Bagaoisan et al. |
| 2005/0033361 A1 | 2/2005 | Galdonik et al. |
| 2005/0049634 A1 | 3/2005 | Chopra |
| 2005/0085773 A1 | 4/2005 | Forsberg |
| 2005/0085851 A1 | 4/2005 | Fiehler et al. |
| 2005/0085852 A1 | 4/2005 | Ditter |
| 2005/0085854 A1 | 4/2005 | Ginn |
| 2005/0085855 A1 | 4/2005 | Forsberg |
| 2005/0085856 A1 | 4/2005 | Ginn |
| 2005/0090860 A1 | 4/2005 | Paprocki |
| 2005/0096697 A1 | 5/2005 | Forsberg et al. |
| 2005/0107826 A1 | 5/2005 | Zhu et al. |
| 2005/0125030 A1 | 6/2005 | Forsberg et al. |
| 2005/0143761 A1 | 6/2005 | Modesitt et al. |
| 2005/0149065 A1 | 7/2005 | Modesitt |
| 2005/0228443 A1 | 10/2005 | Yassinzadeh |
| 2005/0234507 A1 | 10/2005 | Geske et al. |
| 2005/0267520 A1 | 12/2005 | Modesitt |
| 2005/0267522 A1 | 12/2005 | Yassinzadeh et al. |
| 2005/0277980 A1 | 12/2005 | Yassinzadeh |
| 2006/0064159 A1 | 3/2006 | Porter et al. |
| 2006/0079914 A1 | 4/2006 | Modesitt et al. |
| 2006/0111741 A1 | 5/2006 | Nardella |
| 2006/0135990 A1 | 6/2006 | Johnson |
| 2006/0135991 A1 | 6/2006 | Kawaura et al. |
| 2006/0142785 A1 | 6/2006 | Modesitt et al. |
| 2006/0167476 A1 | 7/2006 | Burdulis, Jr. et al. |
| 2006/0206125 A1 | 9/2006 | Fogarty et al. |
| 2006/0235449 A1 | 10/2006 | Schubart et al. |
| 2006/0264975 A1 | 11/2006 | Pipenhagen et al. |
| 2006/0271078 A1 | 11/2006 | Modesitt |
| 2007/0027454 A1 | 2/2007 | Modesitt |
| 2007/0027455 A1 | 2/2007 | Modesitt |
| 2007/0032802 A1 | 2/2007 | Modesitt |
| 2007/0032803 A1 | 2/2007 | Modesitt |
| 2007/0032804 A1 | 2/2007 | Modesitt |
| 2007/0106246 A1 | 5/2007 | Modesitt |
| 2007/0167959 A1 | 7/2007 | Modesitt et al. |
| 2007/0255313 A1 | 11/2007 | Modesitt |

FOREIGN PATENT DOCUMENTS

| | | |
|---|---|---|
| WO | WO-2005/112791 A2 | 12/2005 |
| WO | WO-2006/017023 A2 | 2/2006 |
| WO | WO-2006/124896 A2 | 11/2006 |

OTHER PUBLICATIONS

Franklin, I.J. et al. (1999). "Uptake of Tetracycline by Aortic Aneurysm Wall and Its Effect on Inflammation and Proteolysis," *Brit. J. Surgery* 86(6):771-775.

Pyo, R. et al. (Jun. 2000). "Targeted Gene Disruption of Matrix Metalloproteinase-9 (Gelatinase B) Suppresses Development of Experimental Abdominal Aortic Aneurysms," *J. Clinical Investigation* 105(11):1641-1649.

Tambiah, J. et al. (2001). "Provocation of Experimental Aortic Inflammation and Dilatation by Inflammatory Mediators and *Chlamydia pneumoniae*," *Brit. J. Surgery* 88(7):935-940.

Walton, L.J. et al. (Jul. 6, 1999). "Inhibition of Prostaglandin $E_2$ Synthesis in Abdominal Aortic Aneurysms," *Circulation* 100:48-54.

Xu, Q. et al. (Aug. 11, 2000). "Sp1 Increases Expression of Cyclooxygenase-2 in Hypoxic Vascular Endothelium," *J. Biological Chemistry* 275(32):24583-24589.

Non-Final Office Action mailed Jan. 9, 2009, for U.S. Appl. No. 11/544,317, filed Oct. 6, 2006, 11 pages.

Non-Final Office Action mailed Feb. 18, 2009, for U.S. Appl. No. 11/544,149, filed Oct. 6, 2006, 8 pages.

Non-Final Office Action mailed Feb. 18, 2009, for U.S. Appl. No. 11/545,272, filed Oct. 6, 2006, 7 pages.

Non-Final Office Action mailed Feb. 23, 2009, for U.S. Appl. No. 11/544,196, filed Oct. 6, 2006, 7 pages.

Non-Final Office Action mailed Feb. 23, 2009, for U.S. Appl. No. 11/544,365, filed Oct. 6, 2006, 6 pages.

Non-Final Office Action mailed Feb. 24, 2009, for U.S. Appl. No. 11/544,177, filed Oct. 6, 2006, 7 pages.

International Preliminary Report on Patentability issued on Mar. 3, 2009, for PCT Application No. PCT/US2005/023107, filed on Jun. 30, 2005, five pages.

International Search Report mailed Jun. 5, 2008, for PCT Application No. PCT/US05/23107 filed Jun. 30, 2005, two pages.

International Search Report mailed Aug. 8, 2008, for PCT Application No. PCT/US05/16623 filed May 12, 2005, three pages.

Non-Final Office Action mailed Oct. 8, 2008, for U.S. Appl. No. 11/432,982, filed May 12, 2006, seven pages.

Non-Final Office Action mailed Oct. 29, 2008, for U.S. Appl. No. 11/788,509, filed Apr. 19, 2007, eight pages.

Non-Final Office Action mailed Nov. 12, 2008, for U.S. Appl. No. 10/844,247, filed May 12, 2004, nine pages.

Final Office Action mailed on Jun. 11, 2009, for U.S. Appl. No. 11/432,982, filed on May 12, 2006, seven pages.

International Preliminary Report on Patentability mailed on Mar. 5, 2009, for PCT Application No. PCT/US2005/016623, filed on May 12, 2005, five pages.

International Preliminary Report on Patentability issued on Nov. 14, 2007, for PCT Application No. PCT/US2006/018915, filed on May 12, 2006, five pages.

European Search Report mailed on Jun. 26, 2009, for EP Patent Application No. 08011884.7, filed on May 12, 2005, five pages.

Final Office Action mailed on Jul. 6, 2009, for U.S. Appl. No. 10/844,247, filed on May 12, 2004, fourteen pages.

Final Office Action mailed on Aug. 21, 2009, for U.S. Appl. No. 11/788,509, filed on Apr. 19, 2007, ten pages.

Final Office Action mailed on Aug. 14, 2009, for U.S. Appl. No. 11/544,317, filed on Oct. 6, 2006, eight pages.

International Search Report mailed on Sep. 3, 2009, for PCT Application No. PCT/US2009/051317, filed on Jul. 21, 2009, three pages.

Invitation to Pay Additional Fees mailed on Sep. 10, 2009, for PCT Application No. PCT/US09/51320, filed on Jul. 21, 2009, two pages.

Written Opinion mailed on Aug. 20, 2007, for PCT Application No. PCT/US06/18915, filed on May 12, 2006, four pages.

Written Opinion mailed on Jun. 5, 2008, for PCT Application No. PCT/US05/23107, filed on Jun. 30, 2005, four pages.

Written Opinion mailed on Aug. 8, 2008, for PCT Application No. PCT/US05/16623, filed on May 12, 2005, three pages.

Written Opinion mailed on Sep. 3, 2009, for PCT Application No. PCT/US2009/051317, filed on Jul. 21, 2009, seven pages.

* cited by examiner

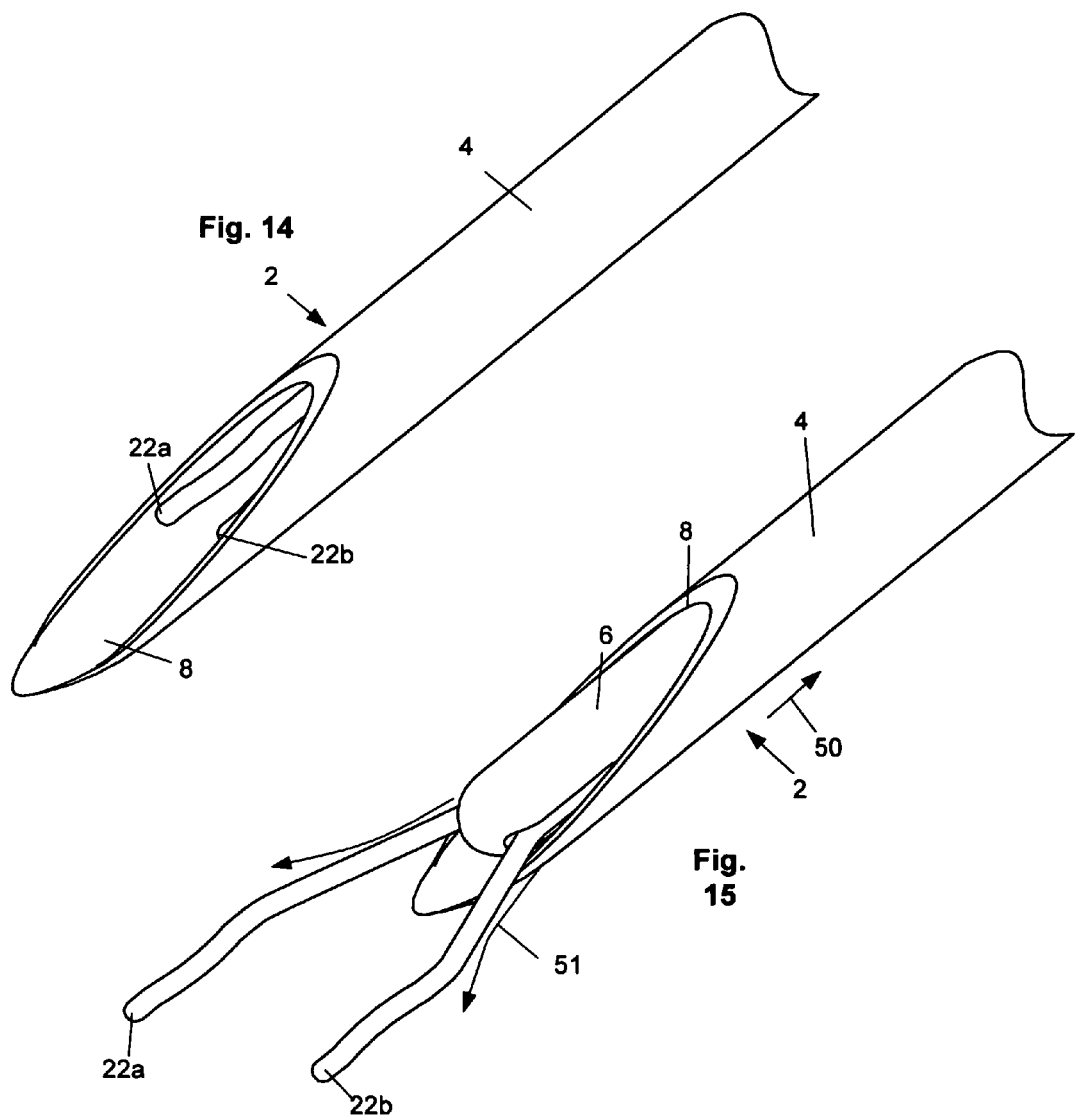

BIOLOGICAL TISSUE CLOSURE DEVICE AND METHOD

BACKGROUND OF THE INVENTION

1. Field of the Invention

The present invention relates to the field of closing openings in biological tissue and methods of performing the same.

2. Description of the Related Art

A number of diagnostic and interventional vascular procedures are now performed translumenally, where a catheter is introduced to the vascular system at a convenient access location—such as the femoral, brachial, or subclavian arteries—and guided through the vascular system to a target location to perform therapy or diagnosis. When vascular access is no longer required, the catheter and other vascular access devices must be removed from the vascular entrance and bleeding at the puncture site must be stopped.

One common approach for providing hemostasis is to apply external force near and upstream from the puncture site, typically by manual compression. This method is time-consuming, frequently requiring one-half hour or more of compression before hemostasis. This procedure is uncomfortable for the patient and frequently requires administering analgesics. Excessive pressure can also present the risk of total occlusion of the blood vessel, resulting in ischemia and/or thrombosis.

After hemostasis is achieved by manual compression, the patient is required to remain recumbent for six to eighteen hours under observation to assure continued hemostasis. During this time bleeding from the vascular access wound can restart, potentially resulting in major complications. These complications may require blood transfusion and/or surgical intervention.

Bioabsorbable fasteners have also been used to stop bleeding. Generally, these approaches rely on the placement of a thrombogenic and bioabsorbable material, such as collagen, at the superficial arterial wall over the puncture site. This method generally presents difficulty locating the interface of the overlying tissue and the adventitial surface of the blood vessel. Implanting the fastener too far from the desired location can result in failure to provide hemostasis. If, however, the fastener intrudes into the vascular lumen, thrombus can form on the fastener. Thrombus can embolize downstream and/or block normal blood flow at the thrombus site. Implanted fasteners can also cause infection and auto-immune reactions/rejections of the implant.

Suturing methods are also used to provide hemostasis after vascular access. The suture-applying device is introduced through the tissue tract with a distal end of the device located at the vascular puncture. Needles in the device draw suture through the blood vessel wall on opposite sides of the punctures, and the suture is secured directly over the adventitial surface of the blood vessel wall to close the vascular access wound.

To be successful, suturing methods need to be performed with a precise control. The needles need to be properly directed through the blood vessel wall so that the suture is well anchored in tissue to provide for tight closure. Suturing methods also require additional steps for the surgeon.

In U.S. Pat. No. 6,656,136 to Weng et al., a hemostatic seal is attempted by the use of high intensity forced ultrasound (HIFU). In commercialized devices utilizing acoustic energy to create hemostasis seals, an acoustic transducer is held near an arteriotomy, and acoustic energy is transmitted to the target location to heat-seal the opening. All other surgical devices are removed from the arteriotomy before application of the acoustic energy. Due to the lack of definite aiming of the acoustic transducer at the arteriotomy, the acoustic energy from the transducer can fail to seal the target arteriotomy, and/or can unintentionally effect surrounding tissue. In addition, the arteriotomy is in the approximate shape of a cylinder, increasing the possibility that walls of the arteriotomy will be too far apart to seal together during energy application.

Due to the deficiencies of the above methods and devices, a need exists for a more reliable vascular closure method and device. There also exists a need for a vascular closure device and method that does not implant a foreign substance and is self-sealing. There also exists a need for a vascular closure device and method requiring no or few extra steps to close the vascular site. Furthermore, there exists a need for a vascular closure device using energy to create a hemostatic seal, where the energy is precisely aimed at the vascular site. Additionally, there exists a need for a vascular closure device using energy to create a hemostatic seal for a vascular opening, where the walls of the vascular opening are brought together before application of the energy.

BRIEF SUMMARY OF THE INVENTION

A device for closing an opening in biological tissue is disclosed. The device has a tensioner and a seal applier. The tensioner is configured to tension the opening. The tensioner can have a first elongated member and a second elongated member. The first elongated member can be configured to bias away from the second elongated member. The second elongated member is configured to bias away from the first elongated member.

The seal applier can have an RF transducer, an acoustic (e.g., ultrasound) transducer, a resistive heater, a microwave heater, an inductive heater, a hole (e.g., a microscopic pore), a web, or combinations thereof. The web can have a first fiber and a second fiber. The first fiber can cross the second fiber. The web can be made from a bioabsorbable material. The web can be removably attached to the device.

Furthermore, a vascular closure device is disclosed. The vascular closure device uses energy to create a hemostatic seal. The device is configured to deliver energy to an arteriotomy. The device is configured to precisely aim the energy at the arteriotomy.

A device for closing an opening in biological tissue is also disclosed. The opening has an internal wall. The device has a wall manipulator, and a seal applier. The wall manipulator is configured to bring a first part of the wall adjacent to a second part of the wall.

A method for closing an opening in a biological tissue is disclosed. The opening has an internal wall. The method includes tensioning the opening and applying a sealer to the opening. Tensioning the opening can include bringing a first part of the wall adjacent to a second part of the wall. The first part of the wall can be brought to less than about 0.51 mm away from the second part of the wall. The first part of the wall can be brought to less than about 0.38 mm away from the second part of the wall. The first part of the wall can be brought to more than about 0.25 mm away from the second part of the wall. The sealer can include energy, such as acoustic energy (e.g., ultrasound), RF energy, conductive heat energy, a liquid adhesive, or combinations thereof.

The method can also include aiming the sealer at the opening. Aiming can include deploying an aiming device into the opening. The aiming device can be on or adjacent to the skin surface. The method can also include deploying a web into the opening. The method can also include leaving the web in the opening at least until the web is entirely bioabsorbed.

Also disclosed is a method for closing an opening in a biological tissue. The opening has an internal wall. The method includes bringing a first part of the wall adjacent to a second part of the wall and applying a sealer to the opening.

BRIEF DESCRIPTION OF THE DRAWINGS

FIG. 14 illustrates a close-up view of the distal end of the closure device of FIG. 11.

FIG. 15 illustrates a close-up view of the distal end of the closure device of FIG. 13.

DETAILED DESCRIPTION

Figure 1:
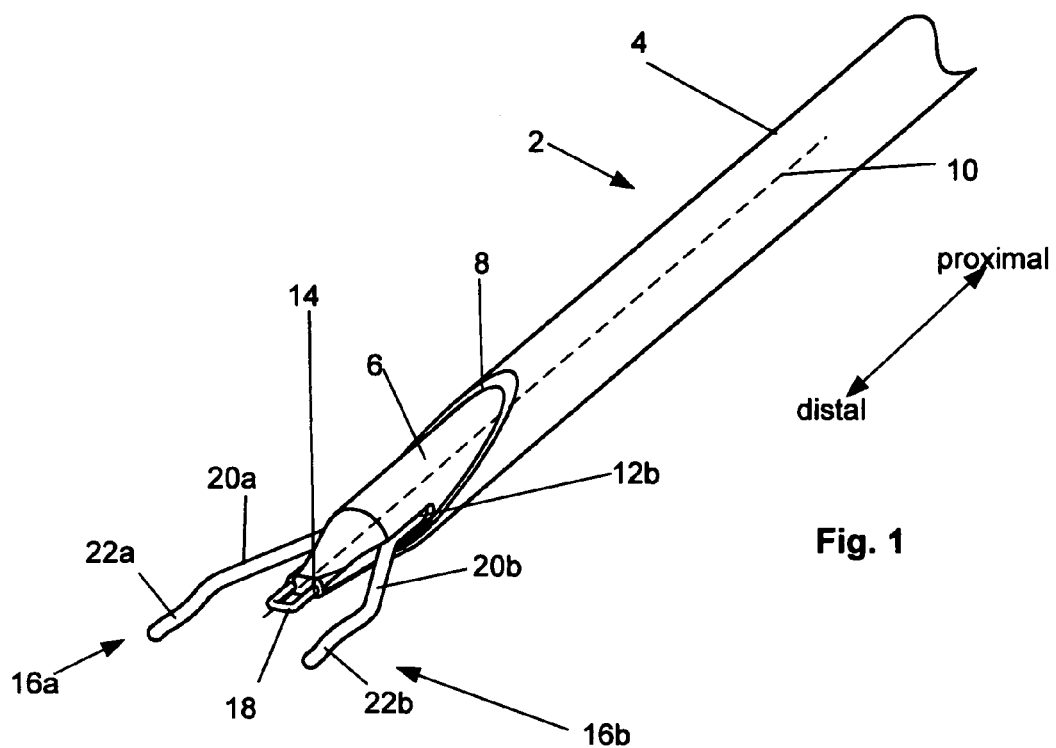
FIG. 1 illustrates an embodiment of the distal end of the closure device.
Figure 2:
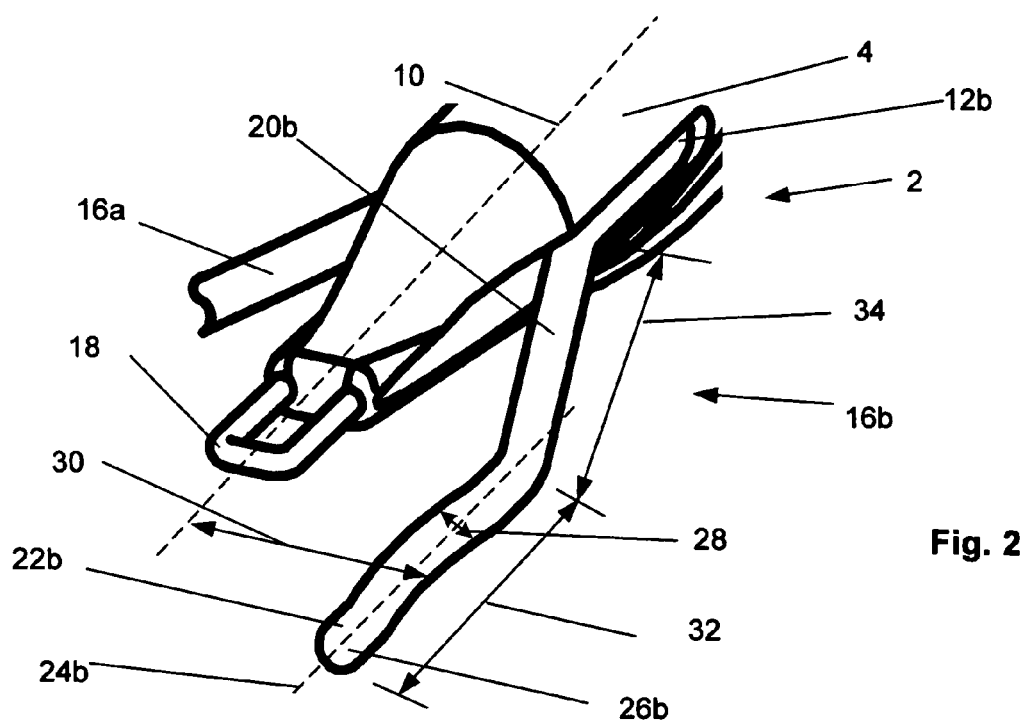
FIG. 2 illustrates a close-up view of FIG. 1 centered around the second expander wire.

FIG. 1 illustrates in an extended (i.e., expanded) configuration, a closure device 2 for biological tissue closure, for example to create hemostasis across an arteriotomy. FIG. 2 illustrates a close-up of the distal end of the closure device of FIG. 1.

The closure device 2 can have a delivery guide 4. The delivery guide 4 can be a tubular member, such as a catheter or sheath on the outer radial side of the closure device 2. The delivery guide 4 can be hollow. In one configuration, the delivery guide 4 can be on the proximal end of the closure device 2. In another configuration, the delivery guide 4 can be the entire length of the closure device 2. The delivery guide 4 can have a low-friction inner surface. The delivery guide 4 can be configured to receive an inner member 6. The delivery guide 4 can have a distal port 8 at the distal end of the delivery guide 4.

The delivery guide 4 can have a proximally-located handle (not shown). The handle can facilitate manipulation of the delivery guide 4 and the inner member 6, and operation of the closure device 2.

The closure device 2 can have the inner member 6. The inner member 6 can be configured to slidably or fixedly attach to the inside of the delivery guide 4. The inner member 6 can have a member longitudinal axis 10. The distal port 8 of the delivery guide 4 can be at a non-perpendicular angle with respect to the member longitudinal axis 10.

The inner member 6 can have a first wire port (not shown) and a second wire port 12b. The wire ports 12a and 12b can be channels along entire length (e.g., from the distal end to the handle at the proximal end) of the member longitudinal axis 10. The wire ports 12a and 12b can have an opening at or near the distal end of the inner member 6.

The inner member 6 can have a sealer channel (not shown). The sealer channel can have an energy conduit and/or a fluid conduit. The sealer channel can be configured to deliver energy (e.g., for tissue adhesion and/or for enhanced cell growth and/or denaturing and recoagulation of the proteins, such as adventitial proteins and/or collagen) and/or a liquid sealant (e.g., a hemostatic agent and/or tissue adhesive and/or volume filler, such as polyethylene glycol (PEG)) to a sealer port 14 at a distal tip of the inner member 6, and/or to one or more elongated members, such as first and/or second expander wires 16a and/or 16b.

A supplemental sealer delivery device 18 can be attached to the sealer port 14. A natural seal can occur due to natural healing of the tissue of the arteriotomy from being in proximity with itself. Supplemental sealing can be any sealing action in addition to the natural seal, including methods to facilitate, maximize, and/or increase the efficiency of the natural sealing. The supplemental sealer delivery device 18, or other delivery device, can be configured to deliver a sealer, for example energy, such as acoustic or radio frequency (RF) energy, microwave energy, and/or a biocompatible adhesive liquid. The supplemental sealer delivery device 18 can be an acoustic transducer, such as a high intensity focus ultrasound (HIFU) transducer or image-guided HIFU. The supplemental sealer delivery device 18 can be from a loop extending from, and returning to, the sealer port 14. The supplemental sealer delivery device 18 can be a spout (not shown) for delivering the liquid sealer. The supplemental sealer delivery device 18 can be a combination of various individual supplemental sealer delivery devices 18 (e.g., an acoustic transducer and a spout).

The first expander wire 16a and the second expander wire 16b can be slidably, and/or rotatably, and/or fixedly attached to the first wire port 12a and second wire port 12b, respectively. The expander wires 16a and 16b can distally extend from the wire ports 12a and 12b, respectively. The first and second expander wires 16a and 16b can have first and second expander wire extensions 20a and 20b, respectively, and first and second expander wire tips 22a and 22b, respectively.

As exemplarily shown on the second expander wire 16b in FIG. 2, the expander wire extensions 20a and 20b can extend radially away from the member longitudinal axis 10. First and second expander wire tips 22a and 22b can extend at angles from the first and second expander wire extensions 20a and 20b, respectively. The first and second expander wire tips 22a and 22b can have tip longitudinal axes 24a and 24b. The first and second tip longitudinal axes 24a and 24b can be substantially parallel with the member longitudinal axis 10. The distal ends of the first and second expander wire tips 22a and 22b can have first (not shown) and second feet 26b, respectively. The feet 26a and 26b can extend radially further from the member longitudinal axis 10 than a main portion of the expander wire tips 22a and 22b.

The expander wires 16a and 16b can have wire diameters 28. The wire diameters 28 can be transverse (i.e., about perpendicular) to the tip longitudinal axes 24a and 24b. The wire diameters 28 can be from about 0.1 mm (0.005 in.) to about 1.2 mm (0.050 in.), for example about 0.38 mm (0.015 in.).

The distance from about the member longitudinal axis 10 to about the radially outer side of the expander wire tips 22a or 22b can be a sealing radius 30. The sealing radius 30 can be from about 0.51 mm (0.020 in.) to about 5.08 mm (0.200 in.), for example about 2.0 mm (0.080 in.).

The expander wire tips 22a and 22b can have tip lengths 32. The tip lengths 32 can be from about 0.51 mm (0.020 in.) to about 25 mm (1.0 in.), for example about 4.06 mm (0.160 in.).

The expander wire extensions 20a and 20b can have extension lengths 34. The extension lengths 34 can be from about 2.54 mm (0.100 in.) to about 25 mm (1.0 in.), for example about 9.65 mm (0.380 in.).

Figure 3:
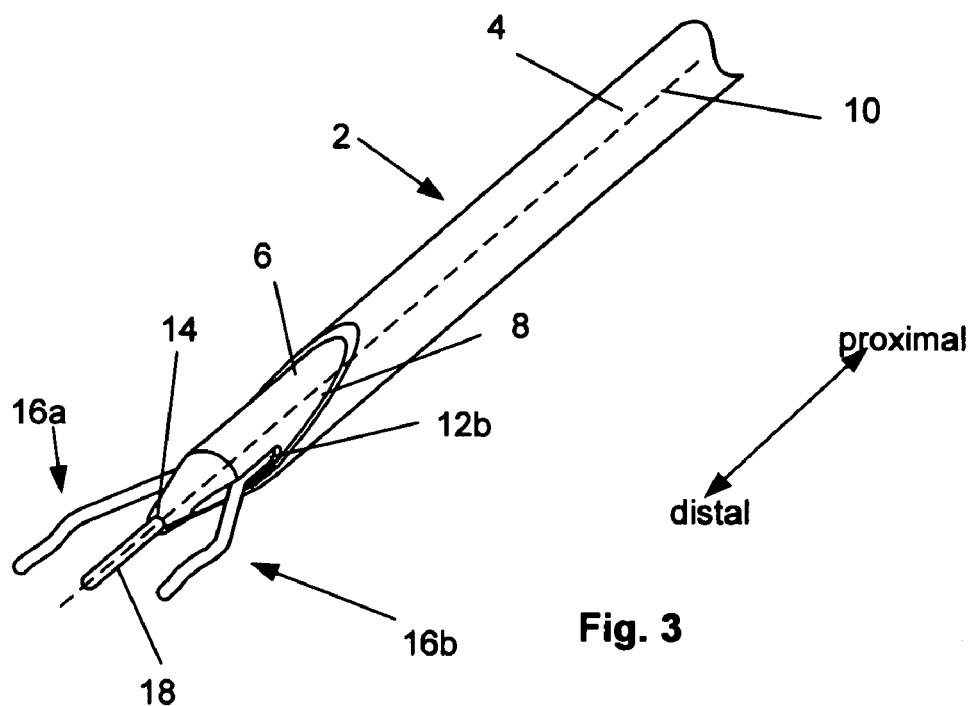
FIGS. 3-6 illustrate various embodiments of the distal end of the closure device.

FIG. 3 illustrates the closure device 2 that can have the supplemental sealer delivery device 18 that can extend from the sealer port 14. The supplemental sealer delivery device 18 can extend along the member longitudinal axis 10 to about the same distance as the distal ends of the first and/or second expander wires 16a and/or 16b are located parallel to the member longitudinal axis 10.

The supplemental sealer delivery device 18 can be configured to transmit RF energy. For example, the supplemental sealer delivery device 18 can be in electrical communication with a conductive wire (e.g., from inside the inner member). The first and/or second expander wires 16a and/or 16b can be configured to transmit RF energy. For example, the first and/or second expander wires 16a and/or 16b can be in electrical communication with a conductive wire (e.g., from inside the inner member 6).

The supplemental sealer delivery device 18 can be configured to transmit microwave energy. For example, the supplemental sealer delivery device 18 can be in electrical communication with a wave guide (e.g., from inside the inner member). The first and/or second expander wires 16a and/or 16b can be configured to transmit microwave energy. For example, the first and/or second expander wires 16a and/or 16b can be in electrical communication with a wave guide (e.g., from inside the inner member 6).

Figure 4:
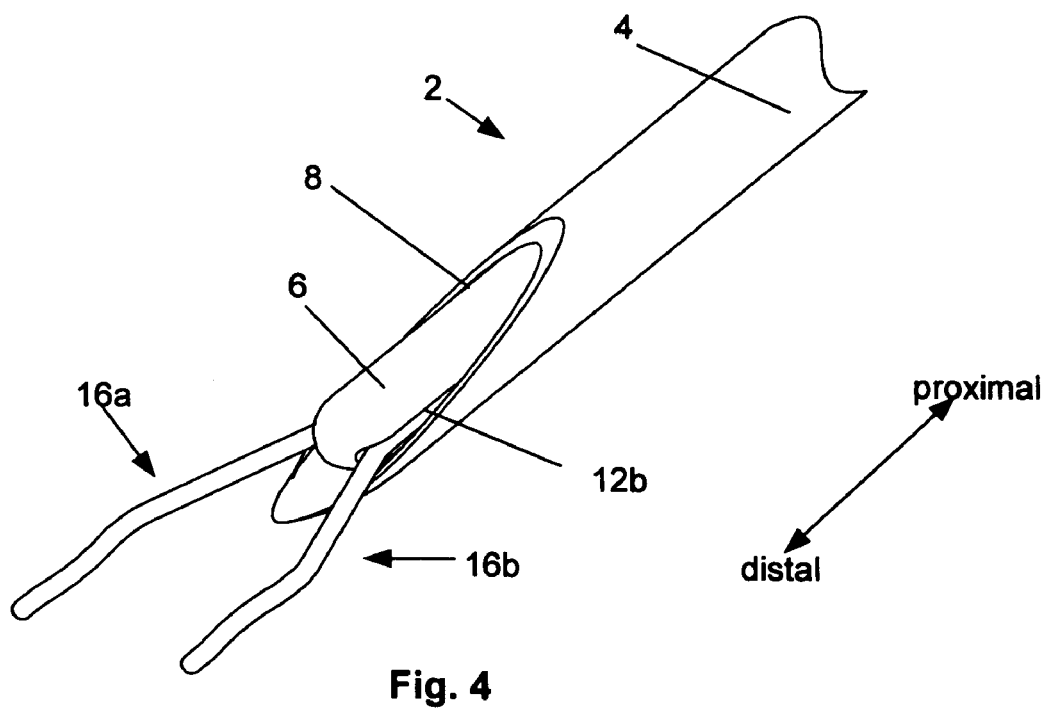

FIG. 4 illustrates the closure device 2 that can have no supplemental sealer delivery device 18. The first and/or second expander wires 16a and/or 16b can be configured to transmit one or more sealers, for example energy. The first and/or second expander wires 16a and/or 16b can be attached to an acoustic energy actuator, for example inside the inner member 6. The first and/or second expander wires 16a and/or 16b can be in electrical communication with a single conductive wire or conductive wires for each expander wire 16a and 16b.

Figure 5:
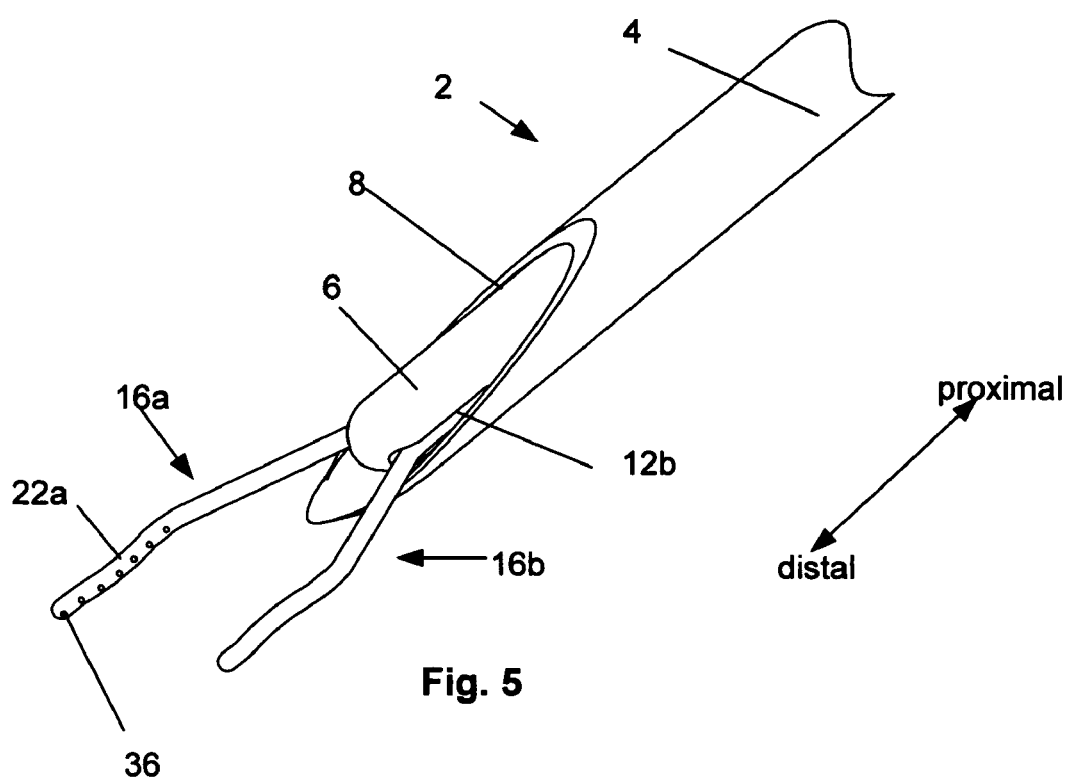

FIG. 5 illustrates the closure device 2 that can have no supplemental sealer delivery device 18. The first and/or second expander wires 16a and/or 16b can be configured to transmit a physical sealer, for example a liquid adhesive sealant. The first and/or second expander wires 16a and/or 16b can be hollow. The first and/or second expander wires 16a and/or 16b can have delivery holes 36 (e.g., microscopic pores and/or macroscopic openings) on the surface thereof, for example to delivery liquid adhesive sealant, or any antibiotic, anesthetic, vaso-restrictors, PEG, or any other agent listed supra or combinations thereof. The delivery holes 36 can be on the first and/or second expander wire tips 22a and/or 22b. The delivery holes 36 can be on the sides of the first and/or second expander wires 16a and/or 16b facing the member longitudinal axis 10. The delivery holes 36 can be arranged along a line, for example parallel to the member longitudinal axis 10. The first and/or second expander wires 16a and/or 16b can be attached, and in fluid communication, at a proximal end to a reservoir, and/or pump, and/or valve holding and/or delivering a sealer, for example a liquid adhesive sealant.

Figure 6:
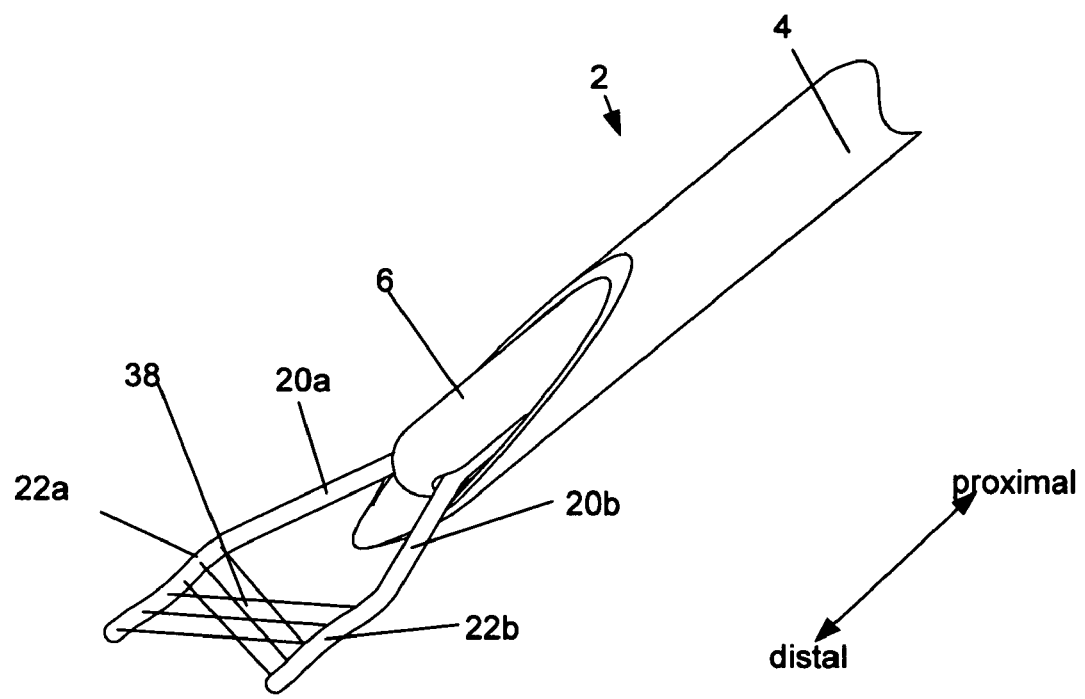

FIG. 6 illustrates the closure device 2 that can have a web 38 that can be attached to the first and second expander wires 16a and 16b. The web 38 can be fixedly or removably attached to the first and second expander wire tips 22a and 22b. The web 38 can be two or more crossed fibers or wires of material. The web 38 can be a mesh. The web 38 can be a porous surface. The web 38 can be made from a metal, and/or a conductive polymer. The web 38 can be made from a resorbable polymer. The web 38 can be configured to transmit RF energy, or can be inductively heated. For example, the web 38 can be in electrical communication with a conductive wire (e.g., via the first and/or second expander wire tip 22a and/or 22b from inside the inner member 6 and/or from along the outside of the delivery guide 4 and/or from another tool not a part of the closure device 2), and/or have current induced therein (e.g., from an external induction coil). The web 38 can be in fluid communication with the delivery holes 36, as shown in FIG. 5. The fibers or wires of the web 38 can be hollow and/or have holes or pores (not shown). The web 38 can be configured to transmit a physical sealer, for example a liquid adhesive sealant.

Figure 7:
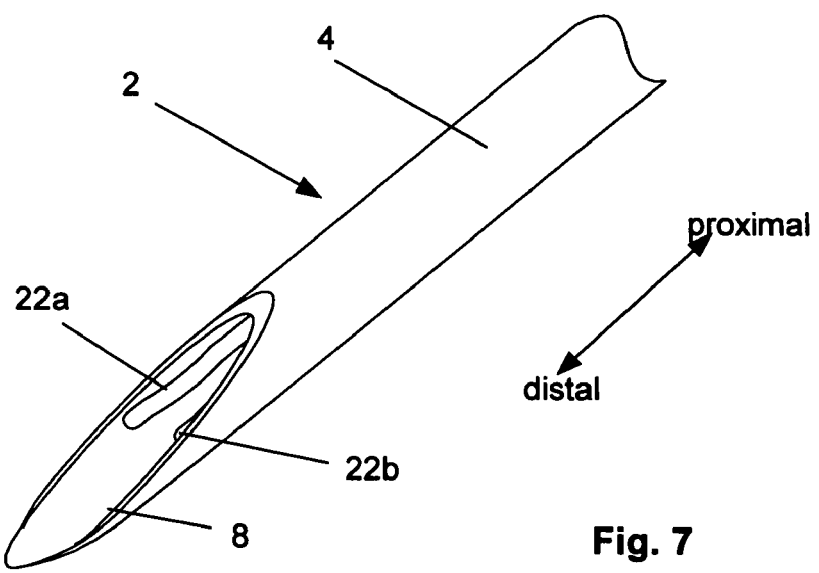
FIG. 7 illustrates an embodiment of the distal end of the closure device in a retracted configuration.

FIG. 7 illustrates the closure device 2 that can have a retracted (i.e., compressed) configuration. The inner member 6 (not shown) can be retracted into the delivery guide 4. The first expander wire 16a and/or the second expander wire 16b can be retracted into the delivery guide 4. The distal ends of the first expander wire 16a and/or the second expander wire 16b can be proximal to the distal port.

Figure 8:
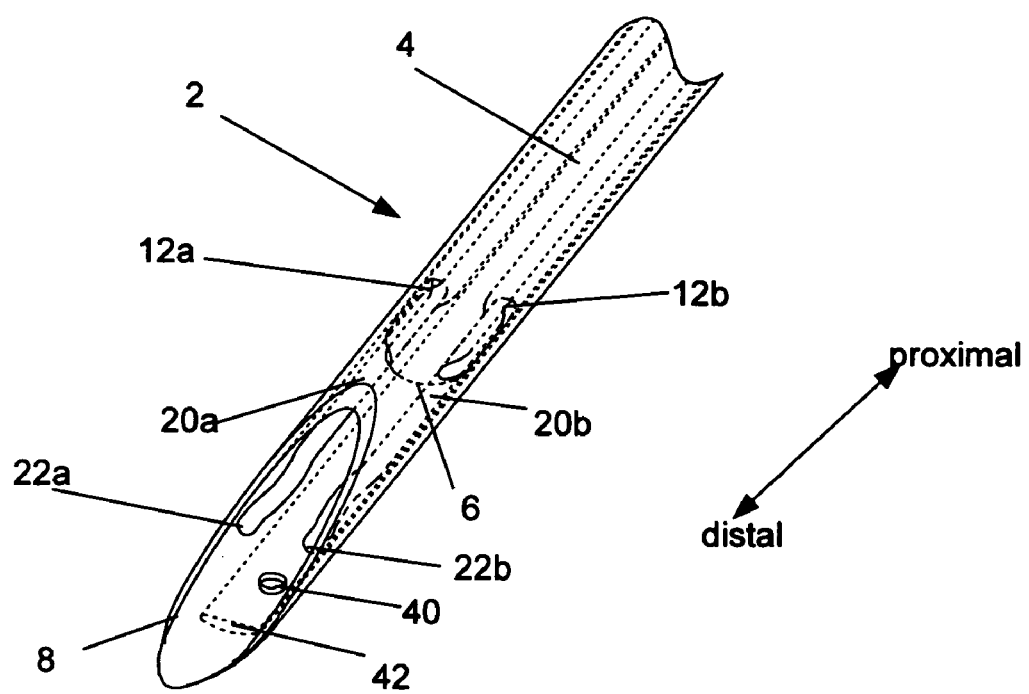
FIGS. 8 and 9 are see-through views of an embodiment of the closure device in a retracted configuration.
Figure 9:
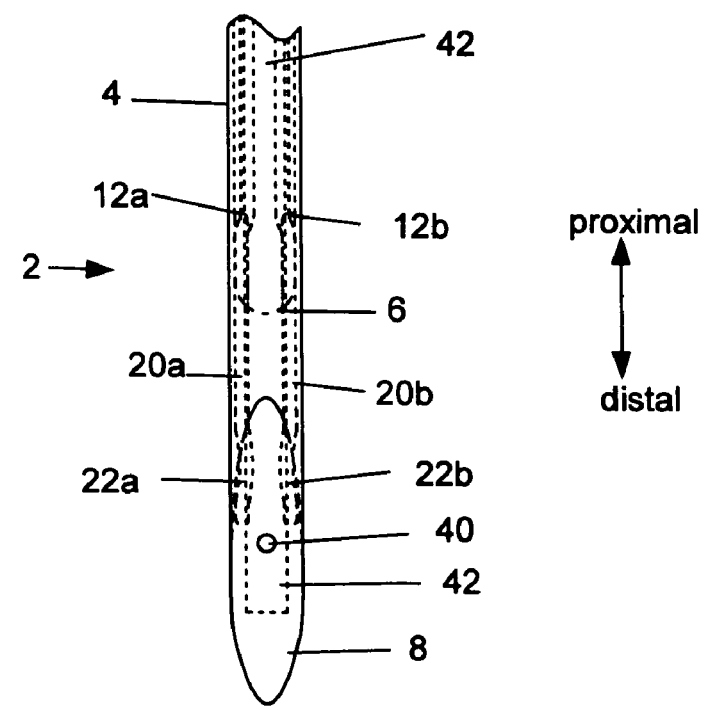

FIGS. 8 and 9 illustrate, in a retracted configuration, the closure device 2 that can check for fluid pressure at the distal port 8. The closure device 2 can have a pressure check port 40 in the delivery guide 4 and/or inner member 6 (not shown). The pressure check port 40 can be distal to the expander wire tips 22a and 22b when the expander wire tips 22a and 22b are in a retracted configuration. The pressure check port 40 can be in fluid communication with the distal port 8 when the closure device 2 is in a retracted position. The pressure check port 40 can be in fluid communication with an outer wall of the delivery guide 4. The pressure check port 40 can be in fluid communication with a pressure check lumen 42. The pressure check lumen 42 can be in fluid communication with a sensor or port on or near the handle (not shown) of the delivery guide 4, such as an external lumen where blood flow can be observed, for example flow from the end of an external tube or port and/or through a transparent or translucent window.

Figure 10:
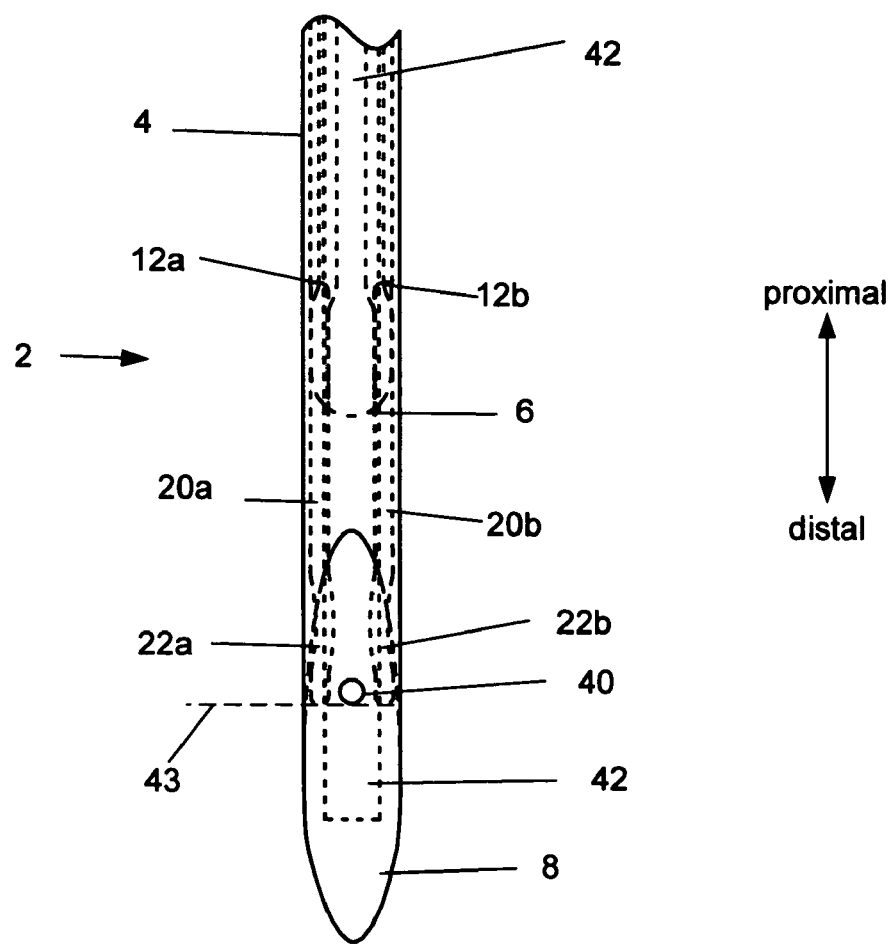
FIG. 10 is a see-through view of an embodiment of the closure device in a retracted configuration.

FIG. 10 illustrates, in a retracted configuration, the closure device 2 that can have the pressure check port 40 aligned with the distal ends of the expander wire tips 22a and 22b, for example, even with a distal alignment line 43.

When the closure device 2 is used, the distal end of the delivery guide 4 can be inserted across the wall of a vessel until a "flash" of blood enters the pressure check port 40, flows up the pressure check lumen 42, and can then be observed by the sensor or port on or near the handle. Once the blood "flash" is observed, the delivery guide 4 can be moved slowly in the proximal direction until the "flash" stops. The "flash" stopping can be an indication of the distal location of the delivery guide (i.e., the pressure check port 40 can be blocked by the lumen wall 54).

Any or all elements of the closure device 2 and/or other devices or apparatuses described herein can be made from, for example, a single or multiple stainless steel alloys, nickel titanium alloys (e.g., Nitinol), cobalt-chrome alloys (e.g., ELGILOY® from Elgin Specialty Metals, Elgin, Ill.; CON- ICHROME® from Carpenter Metals Corp., Wyomissing, Pa.), molybdenum alloys (e.g., molybdenum TZM alloy, for example as disclosed in International Pub. No. WO 03/082363 A2, published 9 Oct. 2003, which is herein incorporated by reference in its entirety), tungsten-rhenium alloys, for example, as disclosed in International Pub. No. WO 03/082363, polymers such as polyester (e.g., DACRON® from E. I. Du Pont de Nemours and Company, Wilmington, Del.), polypropylene, polytetrafluoroethylene (PTFE), expanded PTFE (ePTFE), polyether ether ketone (PEEK), nylon, polyether-block co-polyamide polymers (e.g., PEBAX® from ATOFINA, Paris, France), aliphatic polyether polyurethanes (e.g., TECOFLEX® from Thermedics Polymer Products, Wilmington, Mass.), polyvinyl chloride (PVC), polyurethane, thermoplastic, fluorinated ethylene propylene (FEP), absorbable or resorbable polymers such as polyglycolic acid (PGA), polylactic acid (PLA), polydioxanone, and pseudo-polyamino tyrosine-based acids, extruded collagen, silicone, zinc, echogenic, radioactive, radiopaque materials or combinations thereof. Examples of radiopaque materials are barium sulfate, zinc oxide, titanium, stainless steel, nickel-titanium alloys, tantalum and gold.

Any or all elements of the closure device 2 and/or other devices or apparatuses described herein can be or have a matrix for cell ingrowth or used with a fabric, for example a covering (not shown) that acts as a matrix for cell ingrowth. The matrix and/or fabric can be, for example, polyester (e.g., DACRON® from E. I. Du Pont de Nemours and Company, Wilmington, Del.), polypropylene, PTFE, ePTFE, nylon, extruded collagen, silicone or combinations thereof.

The elements of the closure device 2 and/or other devices or apparatuses described herein and/or the fabric can be filled and/or coated with an agent delivery matrix known to one having ordinary skill in the art and/or a therapeutic and/or diagnostic agent. The agents within these matrices can include radioactive materials; radiopaque materials; cytogenic agents; cytotoxic agents; cytostatic agents; thrombogenic agents, for example polyurethane, cellulose acetate polymer mixed with bismuth trioxide, and ethylene vinyl alcohol; lubricious, hydrophilic materials; phosphor cholene; anti-inflammatory agents, for example non-steroidal anti-inflammatories (NSAIDs) such as cyclooxygenase-1 (COX-1) inhibitors (e.g., acetylsalicylic acid, for example ASPIRIN® from Bayer AG, Leverkusen, Germany; ibuprofen, for example ADVIL® from Wyeth, Collegeville, Pa.; indomethacin; mefenamic acid), COX-2 inhibitors (e.g., VIOXX® from Merck & Co., Inc., Whitehouse Station, N.J.; CELEBREX® from Pharmacia Corp., Peapack, N.J.; COX-1 inhibitors); immunosuppressive agents, for example Sirolimus (RAPAMUNE®, from Wyeth, Collegeville, Pa.), or matrix metalloproteinase (MMP) inhibitors (e.g., tetracycline and tetracycline derivatives) that act early within the pathways of an inflammatory response. Examples of other agents are provided in Walton et al, Inhibition of Prostoglandin $E_2$ Synthesis in Abdominal Aortic Aneurysms, *Circulation, Jul.* 6, 1999, 48-54; Tambiah et al, Provocation of Experimental Aortic Inflammation Mediators and *Chlamydia Pneumoniae, Brit. J. Surgery* 88 (7), 935-940; Franklin et al, Uptake of Tetracycline by Aortic Aneurysm Wall and Its Effect on Inflammation and Proteolysis, *Brit. J. Surgery* 86 (6), 771-775; Xu et al, Sp1 Increases Expression of Cyclooxygenase-2 in Hypoxic Vascular Endothelium, *J. Biological Chemistry* 275 (32) 24583-24589; and Pyo et al, Targeted Gene Disruption of Matrix Metalloproteinase-9 (Gelatinase B) Suppresses Development of Experimental Abdominal Aortic Aneurysms, *J. Clinical Investigation* 105 (11), 1641-1649 which are all incorporated by reference in their entireties.

Method of Manufacture

The elements of the closure device 2 can be directly attached by, for example, melting, screwing, gluing, welding, soldering, abrasing, or use of an interference fit or pressure fit such as crimping, snapping, or combining methods thereof. The elements can be integrated, for example, molding, die cutting, laser cutting, electrical discharge machining (EDM) or stamping from a single piece or material. Any other methods can be used as known to those having ordinary skill in the art.

Integrated parts can be made from pre-formed resilient materials, for example resilient alloys (e.g., Nitinol, ELGILOY®) that are preformed and biased into the post-deployment shape and then compressed into the deployment shape as known to those having ordinary skill in the art.

The expander wires 16a and 16b can be made from pre-formed resilient materials, for example resilient alloys (e.g., Nitinol, ELGILOY®) that are preformed and biased into the post-deployment shape and then compressed into the deployment shape. The post-deployment shape can be the configuration shown in FIG. 2 and elsewhere herein.

Any elements of the closure device 2, or the closure device 2 as a whole after assembly, can be coated by dip-coating, brush-coating or spray-coating methods known to one having ordinary skill in the art. For example, the expander wires 16a and 16b can be spray coated, dip-coated or brushed-coated.

One example of a method used to coat a medical device for vascular use is provided in U.S. Pat. No. 6,358,556 by Ding et al. and hereby incorporated by reference in its entirety. Time release coating methods known to one having ordinary skill in the art can also be used to delay the release of an agent in the coating, for example the coatings on the expander wires 16a and 16b.

Method of Use

Figure 11:
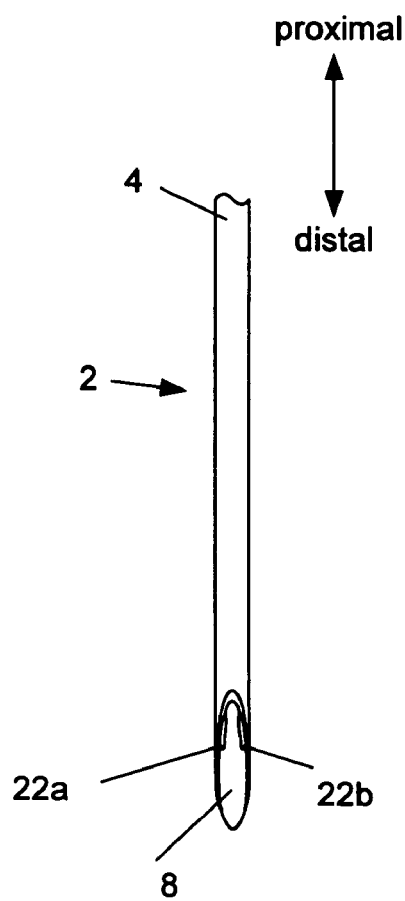
FIGS. 11 through 13 illustrate a method of changing an embodiment of the closure device from a retracted configuration to an extended configuration.
Figure 12:
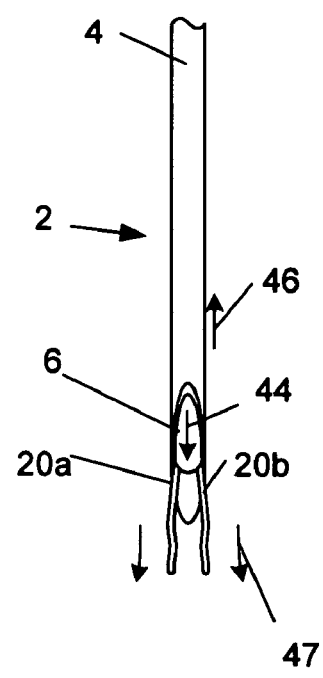
Figure 13:
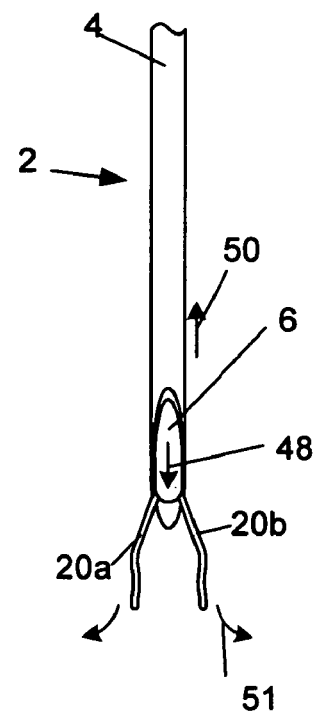

FIGS. 11 through 13 illustrate a method for changing the closure device 2 from a first configuration to a second configuration. FIGS. 14 and 15 also show close-up views of distal ends of the closure device 2 of FIGS. 11 and 13, respectively. As shown in FIGS. 11 and 14, the closure device 2 can be in a fully retracted configuration. The inner member 6 and the expander wires 16a and 16b can be concealed within the delivery guide 4.

As shown in FIG. 12, the closure device 2 can be in a partially deployed configuration. The inner member 6 can be pushed or pulled to be translated, as shown by arrow 44, distally relative to the delivery guide 4, and/or the delivery guide 4 can be pushed or pulled to be translated, as shown by arrow 46, proximally relative to the delivery guide 4.

The delivery guide 4 can restrict (e.g., by interference fit) the expander wires 16a and 16b from expanding away from the member longitudinal axis 10. The expander wires 16a and 16b, can move distally, as shown by arrows 47, relative to the delivery guide 4. The expander wires 16a and 16b can be attached to the inner member 6, such that the inner member 6 pushes the expander wires 16a and 16b when the inner member 6 is pushed.

As shown in FIGS. 13 and 15, the closure device 2 can be in a fully deployed configuration. The inner member 6 can be pushed or pulled to be translated, as shown by arrow 48, distally relative to the delivery guide 4, until the inner member 6 reaches a stop (not shown) with respect to the supplemental sealer delivery device. The stop can be an interference fit between the delivery guide 4 and the inner member 6. The delivery guide 4 can be pushed or pulled to be translated, as shown by arrow 50, proximally relative to the delivery guide 4, until the delivery guide 4 reaches the stop.

The expander wires 16a and 16b, can move distally, as shown by arrows 51, relative to a location at which the expander wires 16a and 16b exit the wire ports 12a and 12b. The location at which the expander wires 16a and 16b exit the respective wire ports 12a and 12b can move beyond the distal port 8 and the delivery guide 4. The expander wires 16a and 16b can expand radially, as shown by arrows 51, away from the member longitudinal axis 10.

Figure 16:
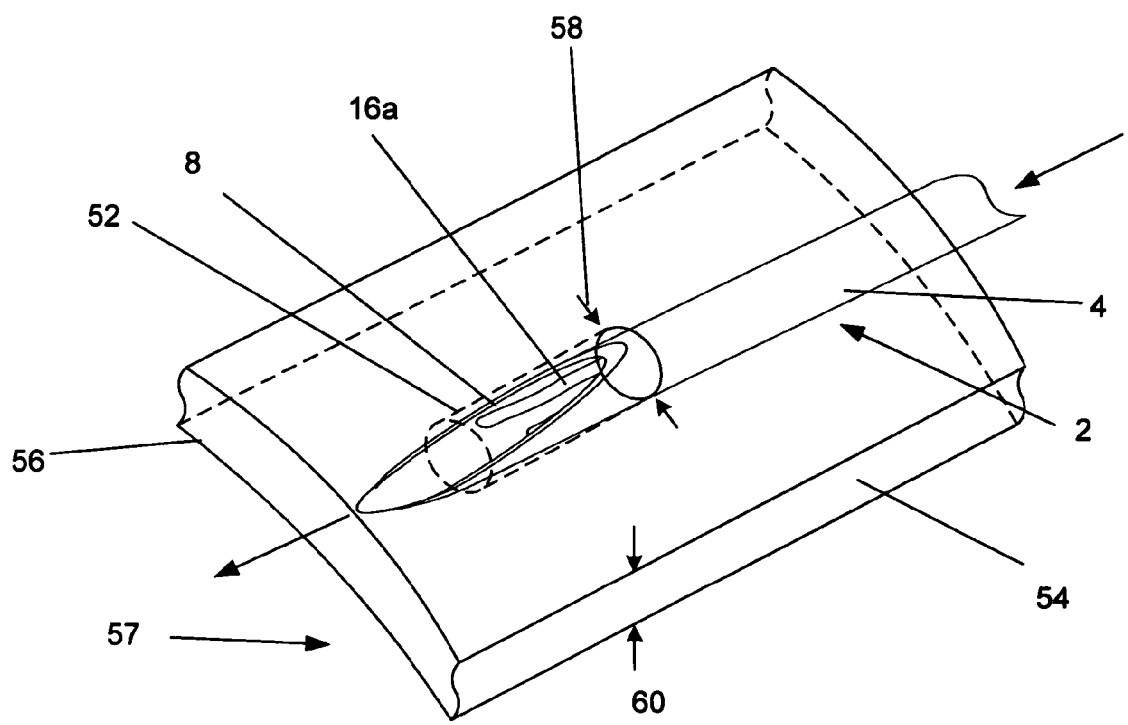
FIGS. 16 and 17 illustrate a method for deploying the expander wires into an arteriotomy in a see-through portion of the lumen wall.

FIG. 16 illustrates that the closure device 2 can be inserted, as shown by arrow, into an opening in tissue, for example the arteriotomy 52 in a lumen wall 54. The closure device 2 can be in the retracted configuration when the closure device 2 is inserted into the arteriotomy 52. After inserting the closure device 2, the distal end of the closure device 2 can be located in or outside and distal to the arteriotomy 52. The lumen wall 54 can have an inner lumen wall surface 56, and can surround a lumen 57.

The arteriotomy 52 can have an arteriotomy diameter 58. The arteriotomy diameter 58 can be from about 0.5 mm (0.020 in.) to about 40 mm (1.5 in.), yet a narrower range from about 1.0 mm (0.040 in.) to about 10.2 mm (0.400 in.), for example about 2.54 mm (0.100 in.). When in the retracted configuration, the closure device 2 can have a diameter smaller than the arteriotomy diameter 58.

The lumen wall 54 can have a lumen wall thickness 60. The lumen wall thickness 60 can be from about 0.51 mm (0.020 in.) to about 5.08 mm (0.200 in.), for example about 1.0 mm (0.040 in.).

Figure 17:
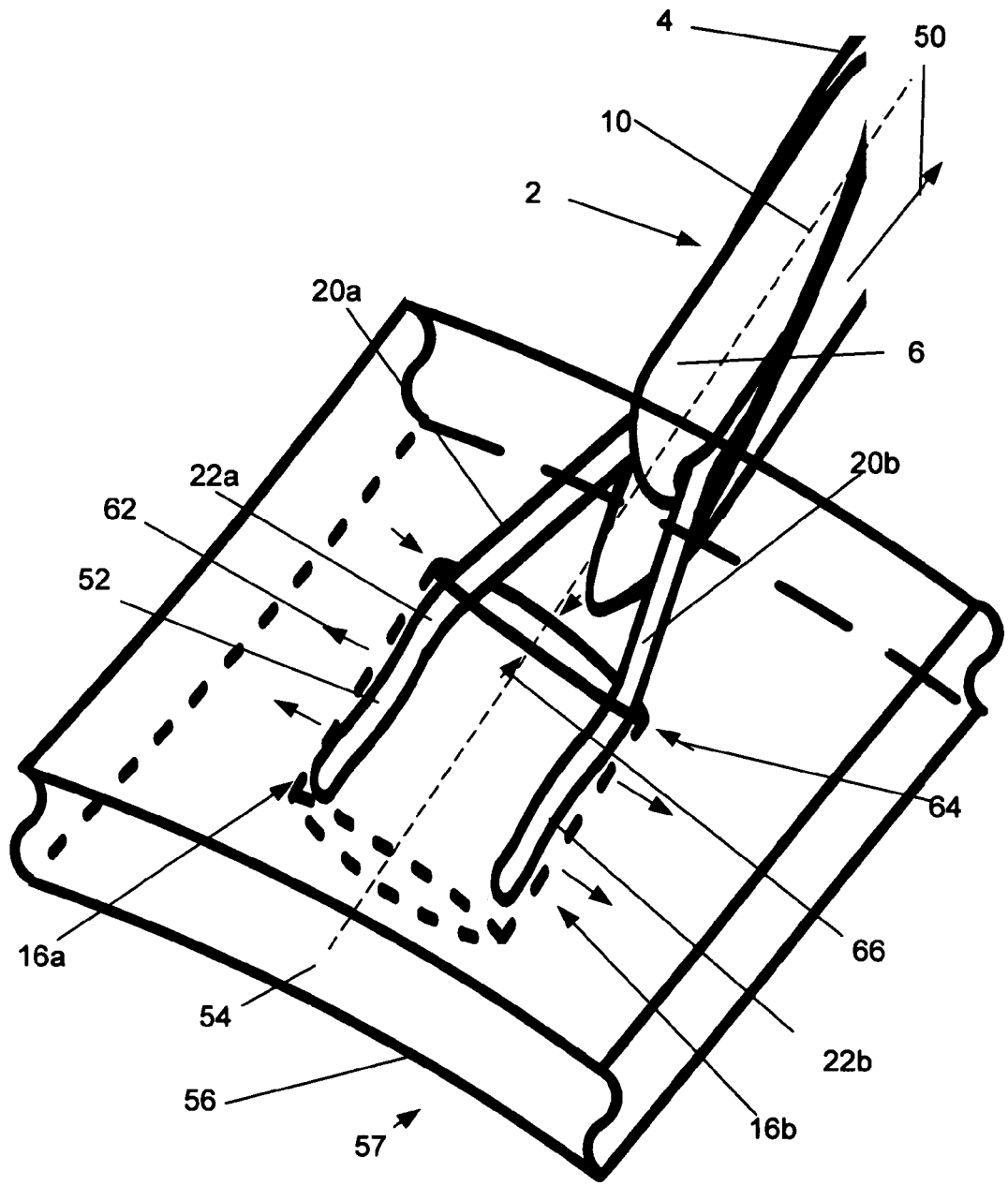
Figure 18:
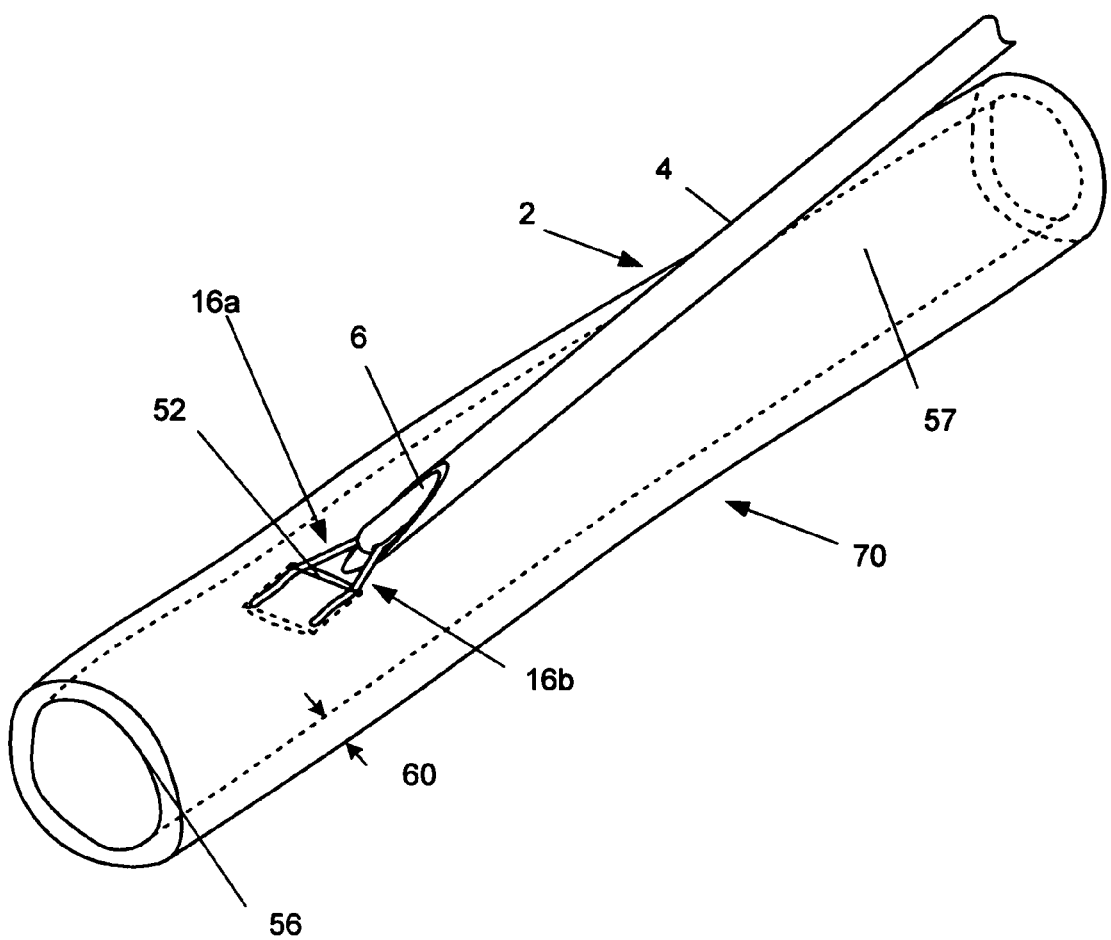
FIG. 18 illustrates a distant view of the method for deploying the expander wires into an arteriotomy in a see-through portion of the lumen wall of FIG. 17.

FIGS. 17 and 18 illustrate expanding the closure device 2 after the closure device 2 has been inserted into the arteriotomy 52. The delivery guide 4 can be moved proximally relative to the inner member 6. The expander wires 16a and 16b can expand, as shown by arrows 62, away from the member longitudinal axis 10. The expander wire tips 22a and 22b can be located inside the arteriotomy 52. The expander wire tips 22a and 22b can expand, for example laterally, against the arteriotomy 52. The arteriotomy 52 can change shape in response to tensioning forces applied by the expander wire tips 22a and 22b, for example, during expansion. The feet 26a and 26b can pressure and/or interference fit with the arteriotomy 52 and/or the inner lumen wall surface 56.

The arteriotomy 52 can have an arteriotomy width 64 and an arteriotomy height 66. The arteriotomy width 64 can be about half the circumference of the arteriotomy 52. The arteriotomy width 64 can be from about 1.0 mm (0.040 in.) to about 10.2 mm (0.400 in.), for example about 4.06 mm (0.160 in.).

The arteriotomy height 66 can be about the wire diameter 28. The arteriotomy height 66 can be less than about 0.51 mm (0.020 in.), more narrowly, less than about 0.38 mm (0.015 in.). The arteriotomy height 66 can be from about 0.1 mm (0.005 in.) to about 1.3 mm (0.050 in.), for example about 0.38 mm (0.015 in.). The arteriotomy height 66 can be small enough to enable cell growth, blood clotting, acoustic sealing, heat sealing, gluing, enhanced self-sealing and combinations thereof across the arteriotomy 52.

Figure 19:
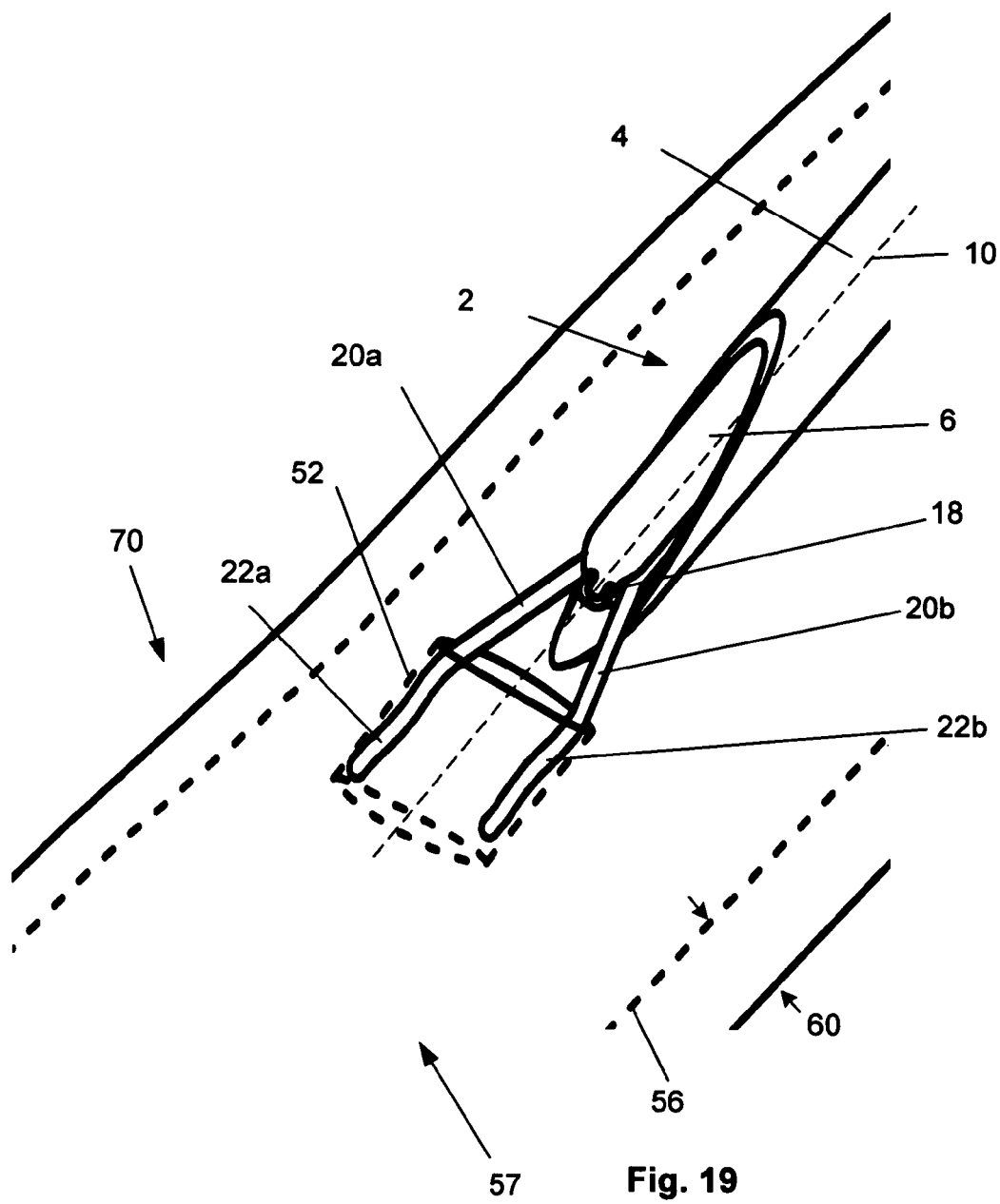
FIGS. 19 through 22 illustrate close-up views of various embodiments for methods of using the closure device in an arteriotomy in a see-through portion of the lumen wall.

FIG. 19 illustrates a method for applying energy (e.g., acoustic) to the tensioned arteriotomy 52. The closure device 2 can have the supplemental sealer delivery device 18. The supplemental sealer delivery device 18 can be an acoustic (e.g., ultrasound) transducer. For example, because the expander wires 16a and 16b can produce opposite forces on opposite sides of the inside of the arteriotomy 52, the supplemental sealer delivery device 18 can be automatically aimed and automatically centered (e.g., aligned along the member longitudinal axis 10 with about the center of the arteriotomy 52). The supplemental sealer delivery device 18 can transmit acoustic energy to the arteriotomy 52.

Figure 20:
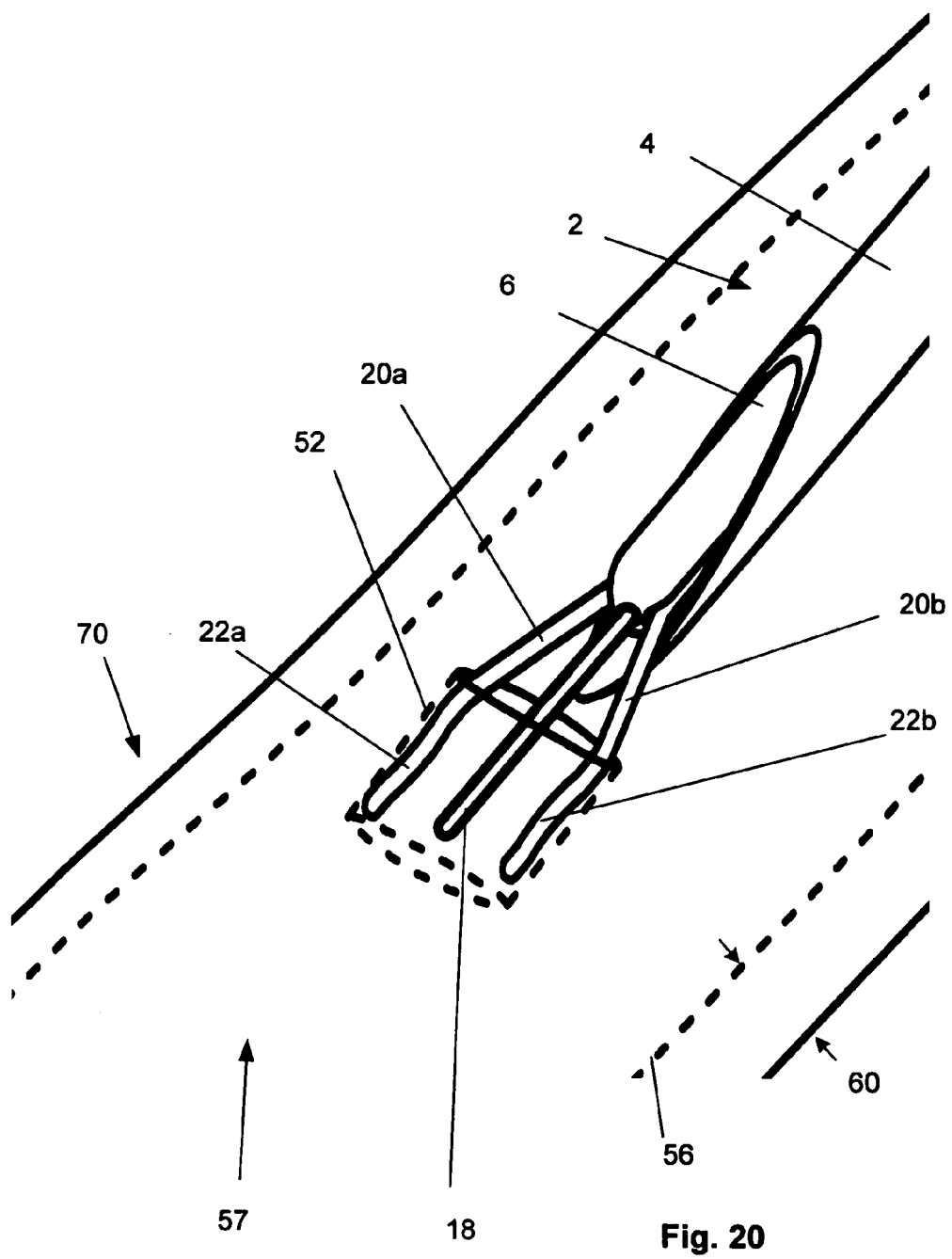

FIG. 20 illustrates a method for applying energy (e.g., RF or microwave) to the tensioned arteriotomy 52. The supplemental sealer delivery device 18 can extend into about the center of the arteriotomy 52. The supplemental sealer delivery device 18 can be an RF transducer. The first and/or second expander wires 16a and/or 16b can be RF or microwave transducers (e.g., microwave antenna). For example, the first and/or second expander wires 16a and/or 16b can be first RF poles, and the supplemental sealer delivery device 18 can be a second RF pole.

Figure 21:
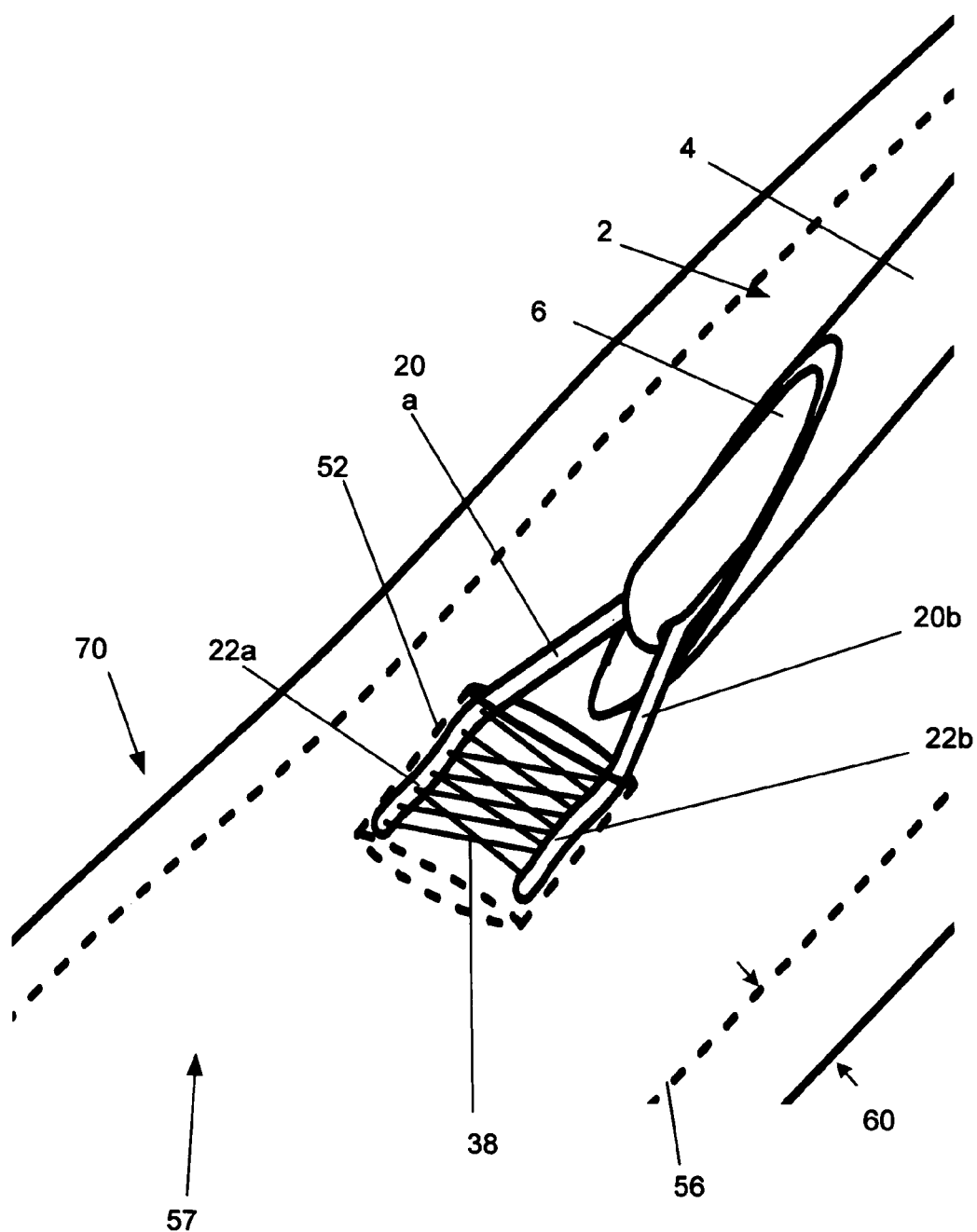

FIG. 21 illustrates a method for applying the sealer (e.g., energy or liquid) into the tensioned arteriotomy 52 using the web 38. The web 38 can be an RF transducer, and/or a resistive heater, and/or an inductive heater and/or microwave heater. The web 38 can be hollow and have holes or pores (not shown). The web 38 can be in fluid communication with a hollow first and/or second expander wires 16a and/or 16b. The web 38 can transfer a liquid, for example a sealer, into the arteriotomy 52.

Once the web 38 applies the sealer to the tensioned arteriotomy 52, the web can be removed from the expander wire tips 22a and 22b, and left in the arteriotomy 52 when the remainder of the closure device 2 is removed. The web 38 can be absorbed by the tissue surrounding the arteriotomy 52.

Figure 22:
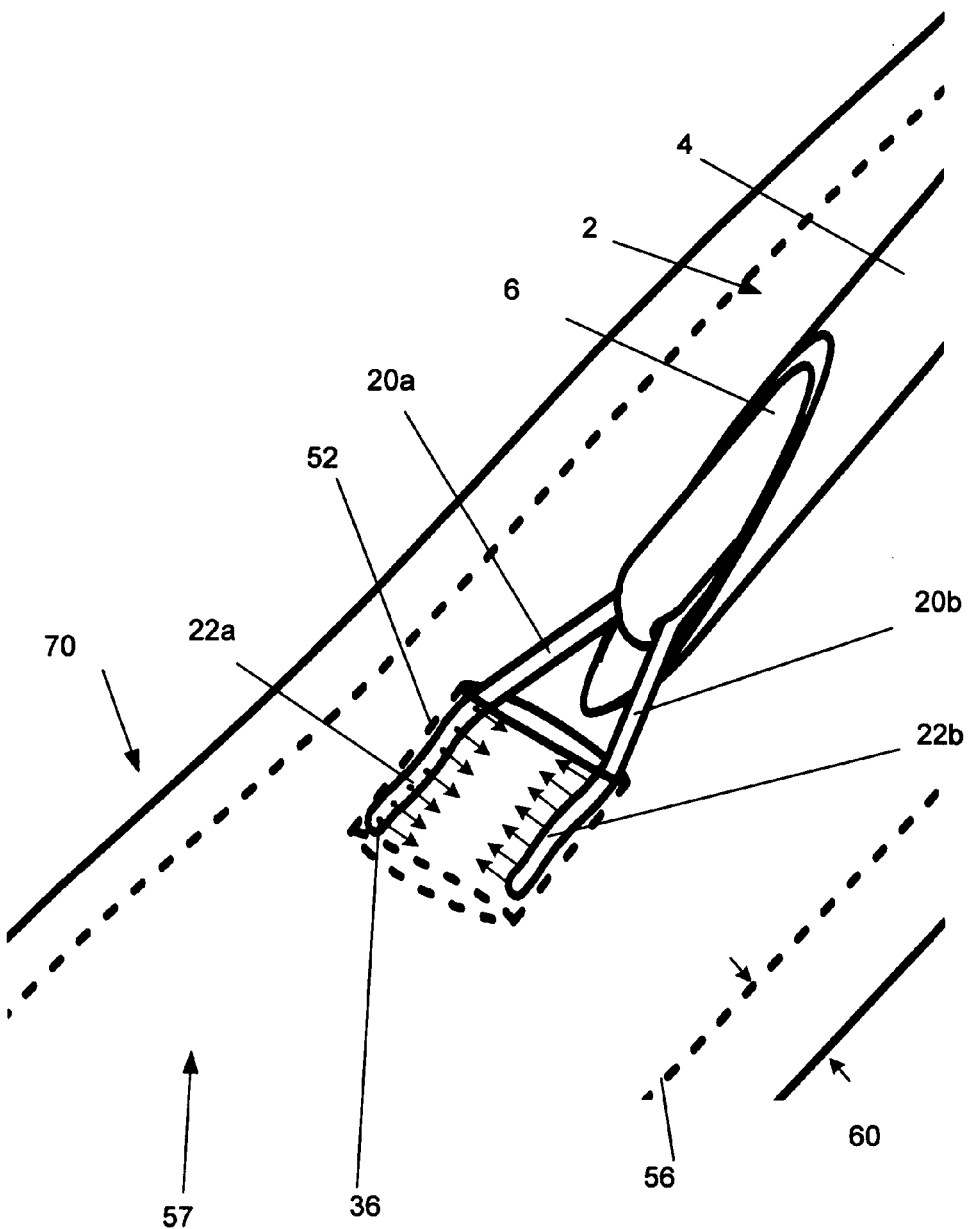

FIG. 22 illustrates a method for applying liquid sealer into the tensioned arteriotomy 52. The liquid sealer can flow, as shown by arrows, from the delivery holes 36 into the arteriotomy 52. Liquid sealers (e.g., biocompatible adhesives, biocompatible epoxies, PEG) for filling and sealing arteriotomies 52 are known to those having ordinary skill in the art. The sealer can act as an adhesive. The adhesive can act as a filler, for example PEG. The sealer can be bioabsorbable.

The arteriotomy 52 can be partially or completely sealed by the energy. Fluid flow can be substantially and/or completely stopped (i.e., hemostasis). Fluid flow through the arteriotomy 52 can be partially or completely sealed by the energy.

The supplemental sealer delivery device 18, and/or the web 38, and/or the expander wire tips 22a and 22b can be electrical resistive heater elements. The sealer can be direct heat transferred through conduction, and/or convection, and/or radiative heating. The supplemental sealer delivery device 18 can heat the arteriotomy directly through conduction.

Any combination of energies, in any proportion, can be applied to the arteriotomy 52. For example, RF or other heating energy can initially be applied to the tensioned arteriotomy 52. The RF or other heating energy can then be stopped and acoustic energy can be applied to the tensioned arteriotomy 52.

Resistive heat energy (i.e., conducted heat generated by electrical resistors) and acoustic energy can be applied simultaneously and in any proportion to the arteriotomy 52. RF energy and resistive heat energy can be applied simultaneously and in any proportion to the arteriotomy 52. Acoustic energy and RF energy can be applied simultaneously and in any proportion to the arteriotomy 52. Acoustic energy and inductive energy can be applied simultaneously and in any proportion to the arteriotomy 52. Resistive heat energy, acoustic energy, RF energy, inductive energy and/or microwave energy can be applied simultaneously and in any proportion to the arteriotomy 52.

Figure 23:
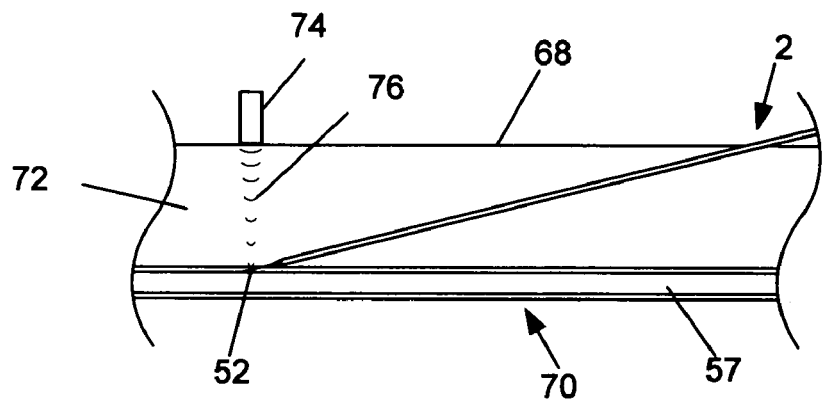
FIG. 23 illustrates a cut-away view of an embodiment for a method of using the closure device with an external transducer.
Figure 24:
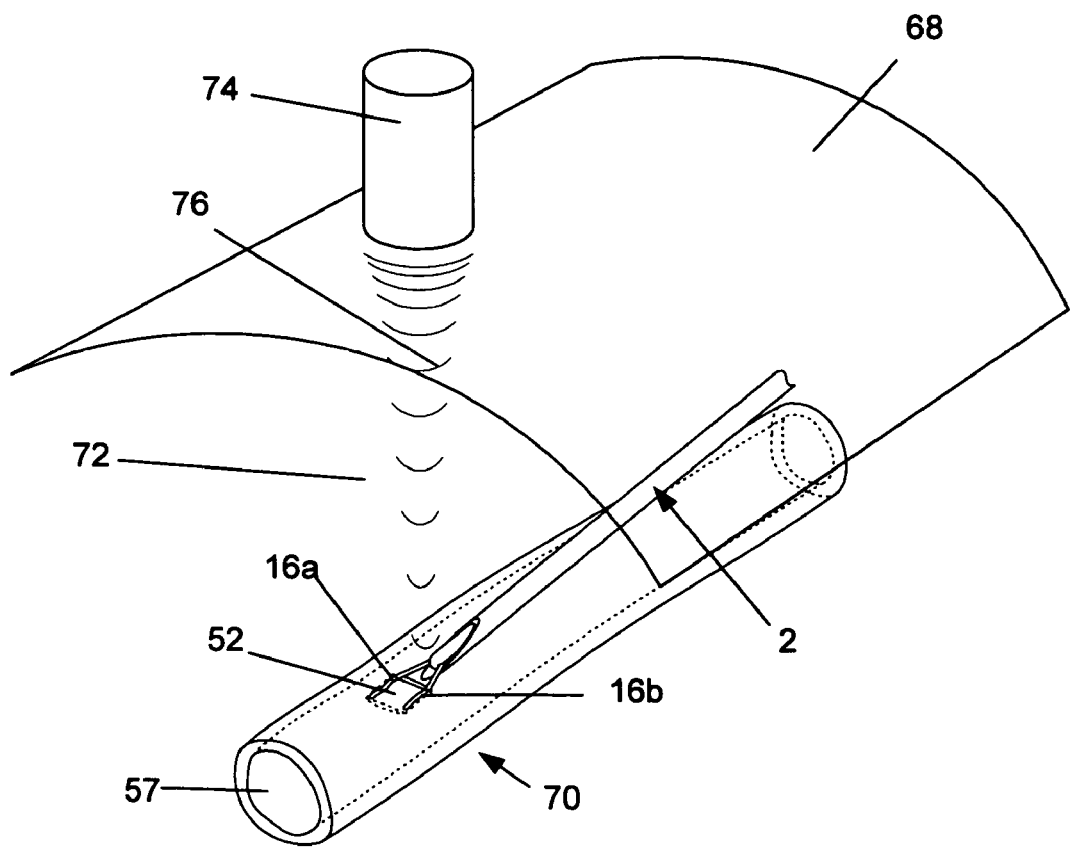
FIG. 24 illustrates a cut-away perspective view of the embodiment of FIG. 23.

FIGS. 23 and 24 illustrate a treatment area that can have skin 68 separated from the vessel 70 by subcutaneous tissue 72 (e.g., fat, muscle, other vessels). An external transducer 74 can be in contact with or adjacent to the skin 68. A gel or other contact supplement known to one having ordinary skill in the art can be sued to improve energy conduction between the external transducer 74 and the skin 68.

After the arteriotomy is substantially sealed, the holes in the lumen wall 54 from which the expander wires 16a and 16b and/or the supplemental sealer delivery device 18 are removed can be inconsequentially small so that bleeding from the holes can be negligible. Sealing (e.g., heating) can be performed as the closure device 2 is removed from the arteriotomy 52 so as to close an holes in the lumen wall 54 formed by the removal of the closure device 2.

The external transducer 74 can be an acoustic transducer, such as an ultrasonic imager, HIFU, image guided HIFU; a radiological transducer, such as an x-ray imager; a magnetic imager, such as a magnetic resonance imager (MRI); therapeutic versions of the aforementioned imagers, or combinations thereof.

The external transducer 74 can be used to send energy waves 76 to the arteriotomy 52. The energy waves 76 can reflect from, transmit through, and/or resonate from the arteriotomy 52 and/or the expander wire tips 22a and 22b. Reflected and/or transmitted and/or resonated energy waves 76 can be received by the external transducer 74 and used to detect the condition (e.g., morphology, structure) and location of the arteriotomy 52 and the expander wire tips 22a and 22b. The external transducer 74 can track the location of the arteriotomy 52 and the expander wire tips 22a and 22b.

The expander wire tips 22a and 22b can have a material or configuration that enhances the ability of the external transducer 74 to detect the expander wire tips 22a and 22b: For example, the expander wire tips 22a and 22b can have an echogenic and/or radiopaque material and/or configuration, such as radiopaque materials listed supra. The first and second expander wire tips 22a and 22b can frame the arteriotomy 52 location and provide a target got an image-guided external transducer 74 (e.g., image guided HIFU). The energy waves 76 can be therapeutic energy, for example used to seal the arteriotomy 52. The energy waves 76 can be focused on the arteriotomy 52, and can transmit minimal energy into surrounding tissue. For example, the energy waves 76 can be therapeutic ultrasound broadcast from a phased array such that a node of the energy waves 76 is located at the arteriotomy 52.

The closure device 2 can be removed from the arteriotomy 52. The closure device 2 can be directly withdrawn from the arteriotomy, for example in a parallel direction with the tip longitudinal axes 24a and 24b. The closure device 2 can be withdrawn from the arteriotomy 52 while the first and second expander wires 16a and 16b are in an expanded configuration.

Before the closure device is withdrawn from the arteriotomy 52, and/or subcutaneous tissue track, the inner member 6 can be retracted into the delivery guide 4, with or without fully retracting the expander wires 16a and 16b into the first and second wire ports 12a and 12b. The delivery guide 4 can be moved distally relative to the inner member 6, reversing the method shown in FIGS. 11 through 16, and changing the closure device 2 into a retracted configuration. The closure device 2 can then be removed from the arteriotomy 52 with the expander wires 16a and 16b in an expanded or retracted configuration.

If the arteriotomy 52 was created by a surgical procedure using a hollow member, such as a catheter, or there is otherwise a catheter in the arteriotomy 52 prior to performing the methods described herein, the already-deployed catheter can be used as the delivery guide 4, or as a sheath for the delivery guide 4.

The closure devices and methods shown and described herein can be used integrally and/or in other combinations with access and closure devices and methods shown and described in U.S. patent application Ser. No. 10/844,247 filed 12 May 2004, and incorporated herein by reference in its entirety. For example, the arteriotomy 52 can be at an angle with respect to the lumen, wherein the angle can be from about 20° to about 90°, more narrowly from about 30° to about 60°, for example about 45°, or otherwise described in U.S. patent application Ser. No. 10/844,247. Also for example, the arteriotomy 52 can have a shape as described by U.S. patent application Ser. No. 10/844,247. The devices and methods described herein can be used in combination with the supplemental closure devices, such as tensioners, clips, toggles, sutures, and combinations thereof, described by U.S. patent application Ser. No. 10/844,247.

It is apparent to one skilled in the art that various changes and modifications can be made to this disclosure, and equivalents employed, without departing from the spirit and scope of the invention. Elements shown with any embodiment are exemplary for the specific embodiment and can be used on other embodiments within this disclosure.

I claim:

1. A method for closing an opening in a biological tissue comprising:
   advancing a tensioning element into the opening, wherein the opening is located between an outer surface and an inner surface of a tissue wall;
   tensioning the opening with the tensioning element in a lateral direction so that the opening collapses in a longitudinal direction; and
   applying a sealer to the opening.

2. The method of claim 1, wherein a first part of the wall is brought to less than about 0.51 mm away from a second part of the wall.

3. The method of claim 1, wherein a first part of the wall is brought to less than about 0.38 mm away from a second part of the wall.

4. The method of claim 1, wherein a first part of the wall is brought to more than about 0.25 mm away from a second part of the wall.

5. The method of claim 1, wherein the sealer comprises energy.

6. The method of claim 5, wherein the energy comprises acoustic energy.

7. The method of claim 6, wherein the energy further comprises RF energy.

8. The method of claim 5, wherein the energy comprises RF energy.

9. The method of claim 5, wherein the energy comprises conductive heat energy.

10. The method of claim 5, wherein the energy comprises inductive heat energy.

11. The method of claim 5, wherein the energy comprises microwave heat energy.

12. The method of claim 1, wherein the sealer comprises an adhesive.

13. The method of claim 1, wherein the sealer comprises a filler.

14. The method of claim 1, wherein the sealer comprises a liquid.

15. The method of claim 12, wherein the adhesive comprises a liquid adhesive.

16. The method of claim 1, further comprising aiming the sealer at the opening.

17. The method of claim 16, wherein aiming comprises deploying an aiming device into the opening.

18. The method of claim 1, further comprising deploying a web into the opening.

19. The method of claim 18, wherein deploying comprises leaving the web in the opening at least for an extended period following closing the opening.

20. The method of claim 19, wherein deploying comprises leaving the web in the opening at least until the web is entirely bioabsorbed.

21. The method of claim 1, wherein at least a portion of the opening is an arteriotomy.

22. The method of claim 1, further comprising inserting a hollow member into the opening, and further performing a first surgical procedure through the hollow member, and wherein tensioning then is performed with the hollow member.

23. A method for closing an opening in a biological tissue, comprising:
   inserting a closure device into the opening;
   bringing a first part of the opening adjacent to a second part of the opening in a longitudinal direction by urging the opening apart in a lateral direction with the closure device while the closure device is positioned within the opening, wherein the opening is located between an outer surface and an inner surface of a tissue wall; and
   applying a sealer to the opening.

24. The method of claim 23, wherein the first part of the opening is brought to less than about 0.51 mm away from the second part of the opening.

25. The method of claim 24, wherein the first part of the opening is brought to less than about 0.38 mm away from the second part of the opening.

26. The method of claim 25, wherein the first part of the opening is brought to more than about 0.25 mm away from the second part of the opening.

27. A method for closing an opening, comprising:
   inserting a first elongated member into the opening;
   inserting a second elongated member into the opening; and
   laterally expanding the opening, wherein expanding comprises applying one or more forces on the opening with the first and second elongated members to expand the opening in a first direction so that the opening closes in a second direction, wherein the opening is located between an outer surface and an inner surface of a tissue wall.

28. The method of claim 27, wherein the opening is an arteriotomy.

* * * * *